(12) United States Patent
Meyer

(10) Patent No.: US 9,102,791 B2
(45) Date of Patent: Aug. 11, 2015

(54) ALKOXYLATED SORBITAN ESTERS AS CRUDE OIL EMULSION BREAKERS

(71) Applicant: Ecolab USA Inc., Naperville, IL (US)

(72) Inventor: G. Richard Meyer, Missouri City, TX (US)

(73) Assignee: Ecolab USA Inc., Naperville, IL (US)

( * ) Notice: Subject to any disclaimer, the term of this patent is extended or adjusted under 35 U.S.C. 154(b) by 131 days.

(21) Appl. No.: 13/753,011

(22) Filed: Jan. 29, 2013

(65) Prior Publication Data

US 2014/0213668 A1 Jul. 31, 2014

(51) Int. Cl.
*C08G 65/26* (2006.01)
*C10G 33/04* (2006.01)
*C07D 307/20* (2006.01)

(52) U.S. Cl.
CPC .......... *C08G 65/2609* (2013.01); *C07D 307/20* (2013.01); *C10G 33/04* (2013.01)

(58) Field of Classification Search
CPC ... C07D 307/20; C08G 65/2609; C10G 33/04
USPC ............ 516/918, 920; 528/418, 419; 549/478
See application file for complete search history.

(56) References Cited

U.S. PATENT DOCUMENTS

| 2,492,473 A | 12/1949 | Fuchs |
| 4,407,707 A * | 10/1983 | Merchant et al. ............. 204/561 |
| 6,984,710 B2 | 1/2006 | Meyer |

* cited by examiner

*Primary Examiner* — Robert Jones, Jr.
(74) *Attorney, Agent, or Firm* — Brinks Gilson & Lione; Eric D. Babych

(57) ABSTRACT

Disclosed herein are alkoxylated sorbitan ester compounds and compositions useful in emulsion breaking applications relating to the production, transportation, storage, and separation of crude oil and natural gas. Also disclosed herein are methods of using the compounds and compositions as emulsion breakers, particularly in applications relating to the production, transportation, storage, and separation of crude oil and natural gas.

10 Claims, No Drawings

ALKOXYLATED SORBITAN ESTERS AS CRUDE OIL EMULSION BREAKERS

TECHNICAL FIELD

The present disclosure relates generally to emulsion breakers, and more particularly to alkoxylated sorbitan esters as emulsion breakers.

BACKGROUND

Formation of emulsions including oil and water commonly occur in the extraction, production and processing/refining of crude oils. The presence of water in crude oil can interfere with refining operations, induce corrosion, increase heat capacity and reduce the handling capacity of pipelines and refining equipment. Consequently, water is often separated from the crude oil in order to effectively process and/or refine the oil. Commonly used emulsion breaking chemicals include alkylphenol formaldehyde resin alkoxylate (AFRA), polyalkylene glycol (PAG), and organic sulfonates. These compounds, however, may not provide satisfactory performance in all instances. Accordingly, there is an ongoing need for new, economical and effective chemicals and processes for resolving emulsions into their component parts of oil and water or brine.

SUMMARY

In one aspect, disclosed are compounds of formula (I),

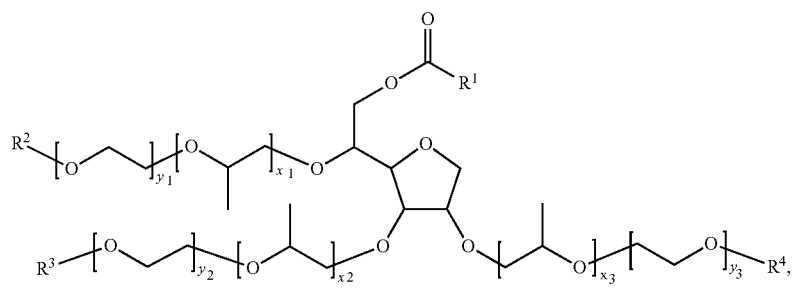

(I)

wherein, $R^1$ is selected from the group consisting of alkyl, alkenyl, and alkynyl;

$R^2$, $R^3$, and $R^4$ are each independently selected from the group consisting of hydrogen, alkyl, alkenyl, alkynyl, aryl, cycloalkyl, heteroaryl, and heterocyclyl;

$x_1+x_2+x_3=x=0.2$ to 75; and $y_1+y_2+y_3=y=0$ to 250.

In another aspect, disclosed are emulsion breaking compositions comprising at least one alkoxylated sorbitan ester of formula (I). In certain embodiments, the emulsion breaking composition contains a pure composition of a compound of formula (I). In other embodiments, the emulsion breaking composition contains a mixture of two or more structurally distinct compounds of formula (I). In certain embodiments, the emulsion breaking composition contains one or more additives.

In another aspect, disclosed are compounds of formula (II),

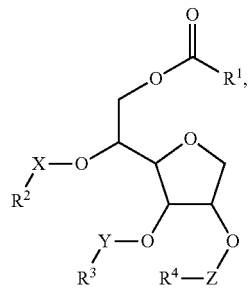

(II)

wherein $R^1$ is selected from the group consisting of alkyl, alkenyl, and alkynyl;

$R^2$, $R^3$, and $R^4$ are each independently selected from the group consisting of hydrogen, alkyl, alkenyl, alkynyl, aryl, cycloalkyl, heteroaryl, and heterocyclyl;

X, Y, and Z, are each independently selected from the group consisting of a bond, a chain consisting of repeating units of formula (a), a chain consisting of repeating units of formula (b), and a chain consisting of a mixture of repeating units of formula (a) and formula (b),

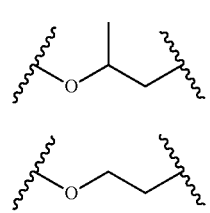

provided that at least one of X, Y, and Z is other than a bond; and provided that the compound of formula (II) comprises at least one repeating unit of formula (a) and at least one repeating unit of formula (b).

In another aspect, disclosed are emulsion breaking compositions comprising at least one alkoxylated sorbitan ester of formula (II). In certain embodiments, the emulsion breaking composition contains a pure composition of a compound of formula (II). In other embodiments, the emulsion breaking composition contains a mixture of two or more structurally distinct compounds of formula (II). In certain embodiments, the emulsion breaking composition contains one or more additives.

In another aspect, disclosed are alkoxylated sorbitan esters prepared by treating a sorbitan ester with propylene oxide and ethylene oxide. In certain embodiments, the alkoxylated sorbitan esters are prepared by treating a sorbitan ester with 0.2-75 molar equivalents of propylene oxide, followed by treatment with 0-250 molar equivalents of ethylene oxide. In certain embodiments, the starting sorbitan ester is selected from the group consisting of sorbitan monolaurate and sorbitan monooleate.

In another aspect, disclosed are methods for breaking an emulsion using a compound or composition of the invention. In certain embodiments, a method of breaking an emulsion comprising oil and water includes adding to the emulsion an effective amount of a compound of formula (I) or formula (II), or any composition thereof. In certain embodiments, the emulsion is a crude oil water-in-oil emulsion, which may optionally be a refinery desalting emulsion or a crude oil production emulsion.

In another aspect, disclosed are processes for preparing alkoxylated sorbitan esters. In certain embodiments, a process for preparing a compound of formula (I) comprises:

treating a sorbitan ester of formula (1) with x equivalents of propylene oxide of formula (2) (e.g., 0.2 to 75 equivalents) to provide a propoxylated sorbitan ester of formula (3),

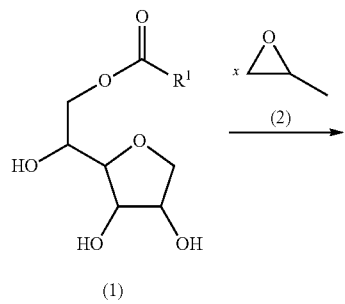

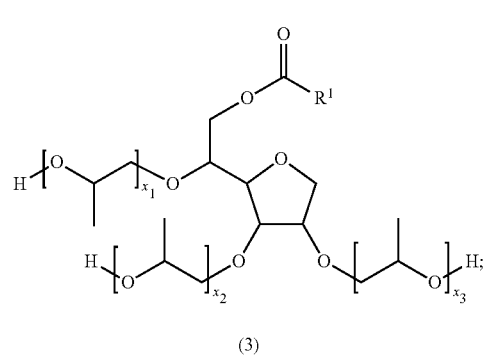

and treating the compound of formula (3) with y equivalents of ethylene oxide of formula (4) (e.g., 0 to 250 equivalents) to provide a compound of formula (I),

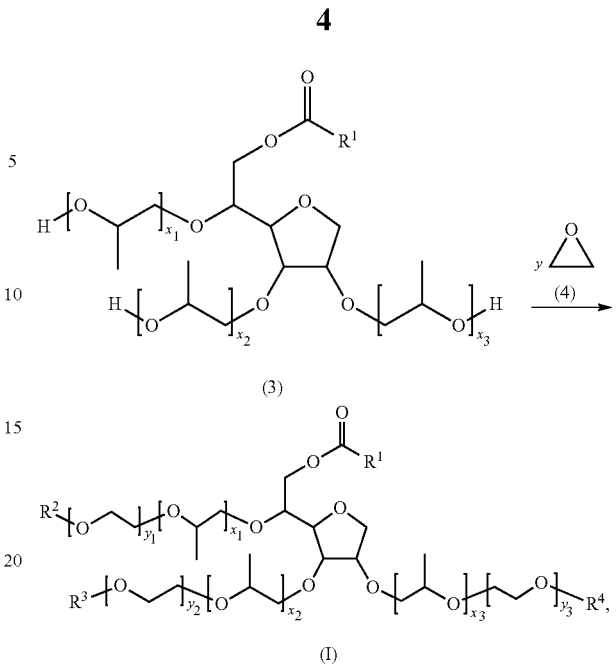

wherein $R^2$, $R^3$, and $R^4$ are each independently hydrogen.

The compounds, compositions, methods and processes are further described herein.

DETAILED DESCRIPTION

Compounds of the invention include alkoxylated sorbitan esters. The alkoxylated sorbitan esters include repeating units derived from propylene oxide and ethylene oxide.

The inventor has surprisingly and unexpectedly discovered that alkoxylated sorbitan esters including repeating units derived from propylene oxide and ethylene oxide, and more particularly alkoxylated sorbitan esters produced by sequential propoxylation-ethoxylation, are useful as emulsion breaking compounds and compositions. Compounds of the invention exhibit multiple properties desirable of emulsion breakers (e.g., rapid water drop, good oil drying), such that the compounds can optionally be used in the absence of other materials to aid demulsification. In contrast, in the current state of the art, crude oil emulsion breakers are generally mixtures of two or more compounds, one of which drops water from the oil, while another dries the oil. Another component may be able to minimize BS or slug values. Thus, it is unusual for a single emulsion breaking material to accomplish more than one of the foregoing as do the compounds and compositions of the present invention.

The inventor has also surprisingly and unexpectedly discovered that compounds of the invention exhibit favorable emulsion breaking properties compared to corresponding ethoxylated compounds lacking propylene oxide units, such as ethoxylated sorbitan esters sold under the trade name TWEEN®.

Finally, compounds of the invention can be efficiently and economically produced and applied as compared to conventional emulsion breakers.

1. DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "suitable substituent," as used herein, is intended to mean a chemically acceptable functional group, preferably a moiety that does not negate the emulsion breaking activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, heterocyclic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. Those skilled in the art will appreciate that many substituents can be substituted by additional substituents.

The term "alkyl," as used herein, refers to a linear or branched hydrocarbon radical, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons. Alkyl groups include, but are not limited to, methyl, ethyl, n-propyl, iso-propyl, n-butyl, iso-butyl, secondary-butyl, and tertiary-butyl. Alkyl groups may be unsubstituted or substituted by one or more suitable substituents, as defined above.

The term "alkenyl," as used herein, refers to a straight or branched hydrocarbon radical, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups may be unsubstituted or substituted by one or more suitable substituents, as defined above.

The term "alkynyl," as used herein, refers to a straight or branched hydrocarbon radical, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, and having one or more carbon-carbon triple bonds. Alkynyl groups include, but are not limited to, ethynyl, propynyl, and butynyl. Alkynyl groups may be unsubstituted or substituted by one or more suitable substituents, as defined above.

The term "alkoxy," as used herein, refers to an alkyl group, as defined herein, appended to the parent molecular moiety through an oxygen atom.

The term "aryl," as used herein, means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above.

The term "carbonyl," "(C=O)," or "—C(O)—" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups may be unsubstituted or substituted by one or more suitable substituents, preferably 1 to 5 suitable substituents, as defined above.

The term "halo" or "halogen," as used herein, refers to a fluoro, chloro, bromo or iodo radical.

The term "heteroaryl," as used herein, refers to a monocyclic, bicyclic, or tricyclic aromatic heterocyclic group containing one or more heteroatoms selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups may be unsubstituted or substituted by one or more suitable substituents, preferably 1 to 5 suitable substituents, as defined above.

The term "heterocycle," as used herein, refers to a monocyclic, bicyclic, or tricyclic group containing 1 to 4 heteroatoms selected from N, O, S(O)$_n$, NH or NR$^x$, wherein IV is a suitable substituent. Heterocyclic groups optionally contain 1 or 2 double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups may be unsubstituted or substituted by one or more suitable substituents, preferably 1 to 3 suitable substituents, as defined above.

The term "hydroxy," as used herein, refers to an —OH group.

The term "oxo," as used herein, refers to a double bonded oxygen (=O) radical wherein the bond partner is a carbon atom. Such a radical can also be thought as a carbonyl group.

The term "water cut," as used herein, means the percentage of water in a composition containing an oil and water mixture.

The term, "water drop," as used herein, means the separation of water from an emulsion, typically a water-in-oil emulsion. Water drop, measured in volume units (e.g., milliliters), may be monitored over a select period of time and compared with similar data obtained from a standard or incumbent chemical. The chemical of choice may drop most or all of the water contained in the emulsion in the shortest period of time. The more complete the "water drop," the drier will be the resulting oil, which may be an important criterion of a good emulsion breaker.

The term, "basic sediment and water" or "(BS&W)," as used herein, means basic sediment, bottoms or base sediment and water. This is a measurement (recorded as volume, even though what is measured may be solid or semi-solid) of solids or sediment found at the bottom of a tube after treatment with a solvent and an emulsion breaker. Low values of BS&W may be desirable, as such values are an indication of the emulsion breaker's ability to keep solids suspended in the oil phase. Low values of BS&W may be desirable as an indication that sediment and solids will not fall out during pipeline transport, avoiding the adverse consequences associated therewith.

The term "myristoleic acid" or "(Z)-tetradec-9-enoic acid," as used herein, refers to

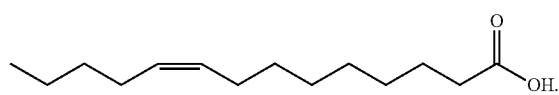 [SMILES: CCCC/C=C\CCCCCCCC(=O)O]

The term "palmitoleic acid" or "(Z)-hexadec-9-enoic acid," as used herein, refers to

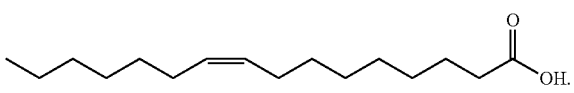

The term "sapienic acid" or "(Z)-hexadec-6-enoic acid," as used herein, refers to

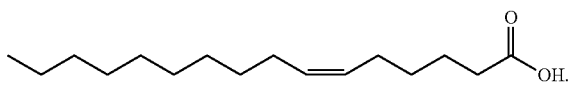 [SMILES: CCCCCCCCC/C=C\CCCCC(=O)O]

The term "oleic acid" or "(Z)-octadec-9-enoic acid," as used herein, refers to

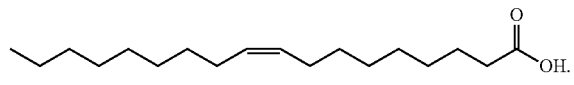 [SMILES: CCCCCCCC/C=C\CCCCCCCC(=O)O]

The term "elaidic acid" or "(E)-octadec-9-enoic acid," as used herein, refers to

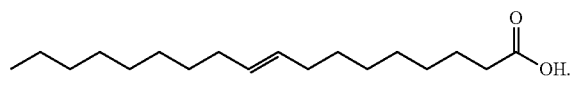 [SMILES: CCCCCCCC/C=C/CCCCCCCC(=O)O]

The term "vaccenic acid" or "(E)-octadec-11-enoic acid," as used herein, refers to

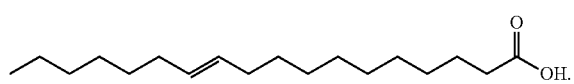 [SMILES: CCCCCC/C=C/CCCCCCCCCC(=O)O]

The term "linoleic acid" or "(9Z,12Z)-octadeca-9,12-dienoic acid," as used herein, refers to

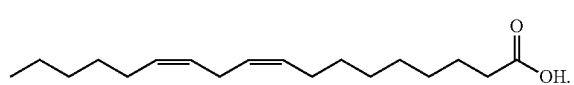 [SMILES: CCCCC/C=C\C/C=C\CCCCCCCC(=O)O]

The term "linoelaidic acid" or "(9E,12E)-octadeca-9,12-dienoic acid," as used herein, refers to

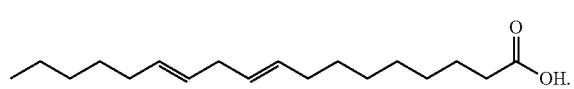 [SMILES: CCCCC/C=C/C/C=C/CCCCCCCC(=O)O]

The term "α-linolenic acid" or "(9Z,12Z,15Z)-octadeca-9,12,15-trienoic acid," as used herein, refers to

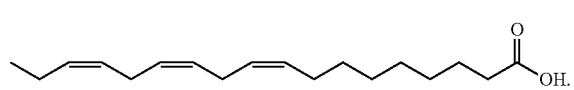

The term "arachidonic acid" or "(5Z,8Z,11Z,14Z)-icosa-5,8,11,14-tetraenoic acid," as used herein, refers to

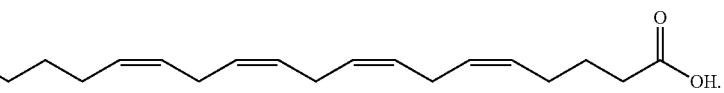

The term "eicosapentaenoic acid" or "(5Z,8Z,11Z,14Z,17Z)-icosa-5,8,11,14,17-pentaenoic acid," as used herein, refers to

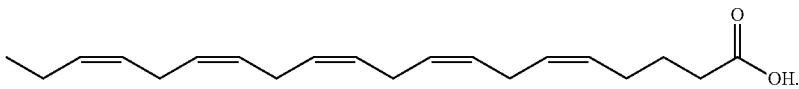

The term "erucic acid" or "(Z)-docos-13-enoic acid," as used herein, refers to

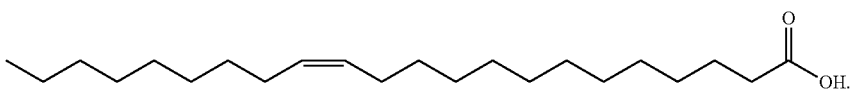 [SMILES: CCCCCCCC/C=C\CCCCCCCCCCCC(=O)O]

The term "docosahexaenoic acid" or "(4Z,7Z,10Z,13Z,16Z,19Z)-docosa-4,7,10,13,16,19-hexaenoic acid," as used herein, refers to

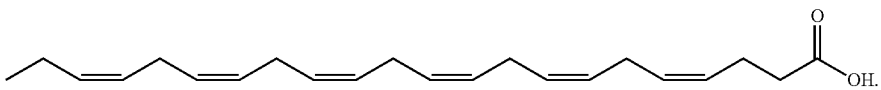 [SMILES: CC/C=C\C/C=C\C/C=C\C/C=C\C/C=C\C/C=C\CCC(=O)O]

The term "hexadecatrienoic acid" or "(7Z,10Z,13Z)-hexadeca-7,10,13-trienoic acid," as used herein, refers to

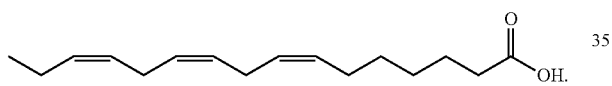

The term "stearidonic acid" or "(6Z,9Z,12Z,15Z)-octadeca-6,9,12,15-tetraenoic acid," as used herein, refers to

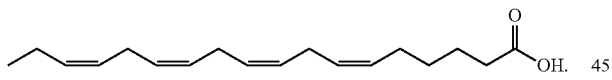

The term "eicosatrienoic acid" or "(11Z,14Z,17Z)-icosa-11,14,17-trienoic acid," as used herein, refers to

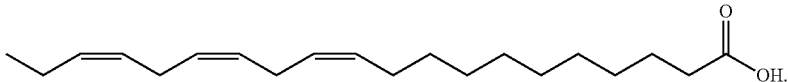 [SMILES: CC/C=C\C/C=C\C/C=C\CCCCCCCCCC(=O)O]

The term "eicosatetraenoic acid" or "(5Z,8Z,11Z,14Z,17Z)-icosa-5,8,11,14,17-pentaenoic acid," as used herein, refers to

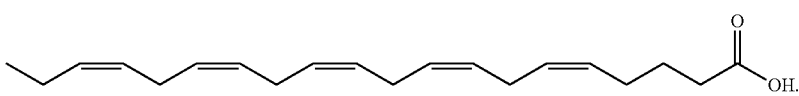

The term "heneicosapentaenoic acid" or "(6Z,9Z,12Z, 15Z,18Z)-henicosa-6,9,12,15,18-pentaenoic acid," as used herein, refers to

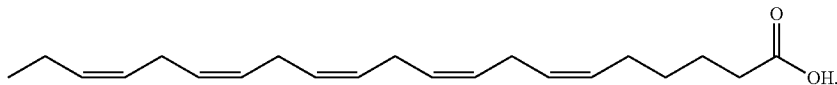

The term "clupanodonic acid" or "(7Z,10Z,13Z,16Z,19Z)-docosa-7,10,13,16,19-pentaenoic acid," as used herein, refers to

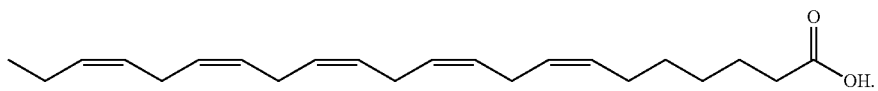 [SMILES: CC/C=C\C/C=C\C/C=C\C/C=C\C/C=C\CCCCCC(=O)O]

The term "osbond acid" or "(4Z,7Z,10Z,13Z,16Z)-docosa-4,7,10,13,16-pentaenoic acid," as used herein, refers to

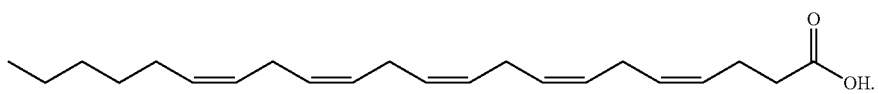 [SMILES: CCCCC/C=C\C/C=C\C/C=C\C/C=C\C/C=C\CCC(=O)O]

The term "(9Z,12Z,15Z,18Z,21Z)-tetracosa-9,12,15,18,21-pentaenoic acid," as used herein, refers to

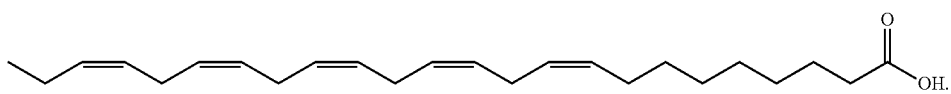 [SMILES: CC/C=C\C/C=C\C/C=C\C/C=C\C/C=C\CCCCCCCC(=O)O]

The term "nisinic acid" or "(6Z,9Z,12Z,15Z,18Z,21Z)-tetracosa-6,9,12,15,18,21-hexaenoic acid," as used herein, refers to

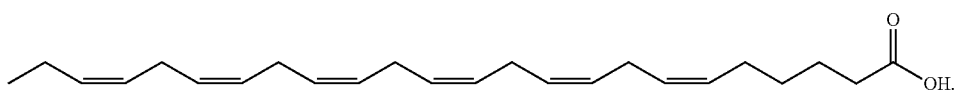

The term "γ-linolenic acid" or "(6Z,9Z,12Z)-octadeca-6,9,12-trienoic acid," as used herein, refers to

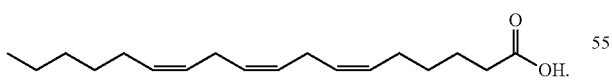

The term "eicosadienoic acid" or "(11Z,14Z)-icosa-11,14-dienoic acid," as used herein, refers to

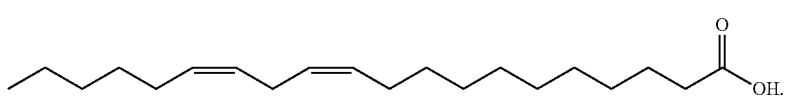 [SMILES: CCCCC/C=C\C/C=C\CCCCCCCCCC(=O)O]

The term "dihomo-γ-linolenic acid" or "(8Z,11Z,14Z)-icosa-8,11,14-trienoic acid," as used herein, refers to

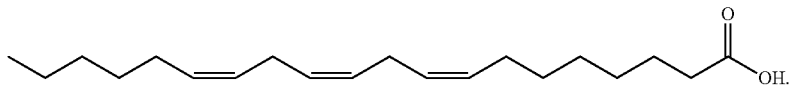 [SMILES: CCCCC/C=C\C/C=C\C/C=C\CCCCCCC(=O)O]

The term "docosadienoic acid" or "(13Z,16Z)-docosa-13,16-dienoic acid," as used herein, refers to

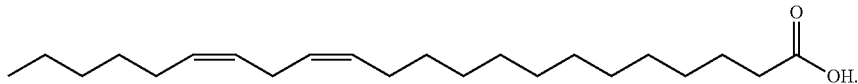

The term "adrenic acid" or "(7Z,10Z,13Z,16Z)-docosa-7,10,13,16-tetraenoic acid," as used herein, refers to

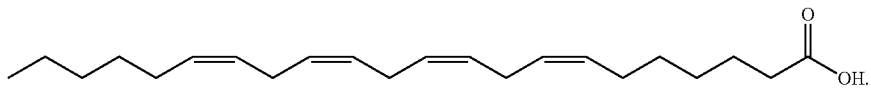 [SMILES: CCCCC/C=C\C/C=C\C/C=C\C/C=C\CCCCCC(=O)O]

The term "tetracosatetraenoic acid" or "(9Z,12Z,15Z,18Z)-tetracosa-9,12,15,18-tetraenoic acid," as used herein, refers to

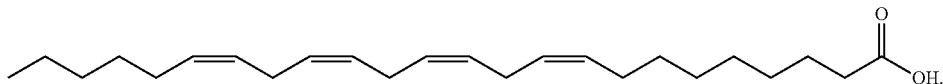 [SMILES: CCCCC/C=C\C/C=C\C/C=C\C/C=C\CCCCCCCC(=O)O]

The term "(6Z,9Z,12Z,15Z,18Z)-tetracosa-6,9,12,15,18-pentaenoic acid," as used herein, refers to

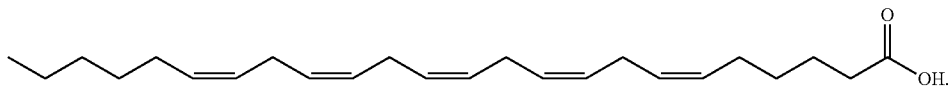 [SMILES: CCCCC/C=C\C/C=C\C/C=C\C/C=C\C/C=C\CCCCC(=O)O]

The term "(Z)-Eicos-11-enoic acid" or "(Z)-icos-11-enoic acid," as used herein, refers to

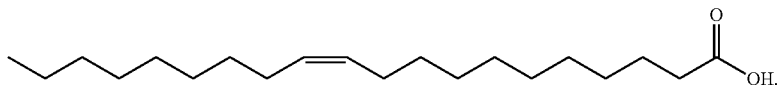 [SMILES: CCCCCCCC/C=C\CCCCCCCCCC(=O)O]

The term "paullinic acid" or "(Z)-icos-13-enoic acid," as used herein, refers to

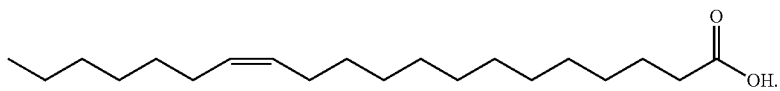 [SMILES: CCCCCC/C=C\CCCCCCCCCCCC(=O)O]

The term "mead acid" or "(5Z,8Z,11Z)-Eicosa-5,8,11-trienoic acid," as used herein, refers to The term "nervonic acid," or "(Z)-tetracos-15-enoic acid," as used herein, refers to

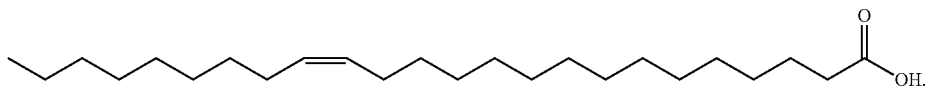 [SMILES: CCCCCCCC/C=C\CCCCCCCCCCCCCC(=O)O]

The term "rumenic acid" or "(9Z,11E)-octadeca-9,11-dienoic acid," as used herein, refers to

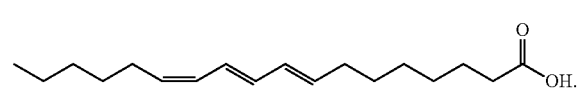 [SMILES: CCCCC\C=C/C=C/C=C/CCCCCCC(=O)O]

The term "α-calendic acid" or "(8E,10E,12Z)-octadeca-8,10,12-trienoic acid," as used herein, refers to

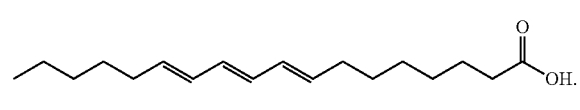 [SMILES: CCCCC/C=C/C=C/C=C/CCCCCCC(=O)O]

The term "β-calendic acid" or "(8E,10E,12E)-octadeca-8,10,12-trienoic acid," as used herein, refers to

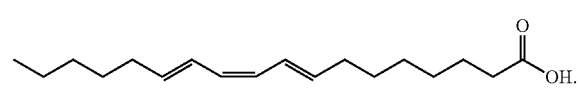 [SMILES: CCCCC/C=C/C=C\C=C\CCCCCCC(=O)O]

The term "jacaric acid" or "(8E,10Z,12E)-octadeca-8,10,12-trienoic acid,"

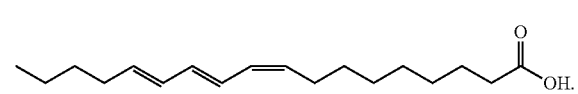 [SMILES: CCCC/C=C/C=C/C=C\CCCCCCCC(=O)O]

The term "α-eleostearic acid" or "(9Z,11E,13E)-octadeca-9,11,13-trienoic acid," as used herein, refers to

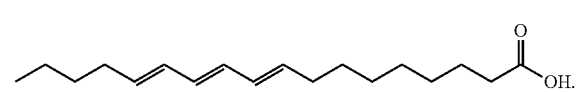 [SMILES: CCCC/C=C/C=C/C=C/CCCCCCCC(=O)O]

The term "β-eleostearic acid" or "(9E,11E,13E)-octadeca-9,11,13-trienoic acid," as used herein, refers to

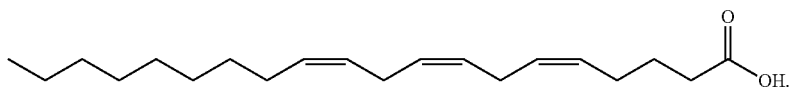

The term "catalpic acid" or "(9E,11E,13Z)-octadeca-9,11,13-trienoic acid," as used herein, refers to

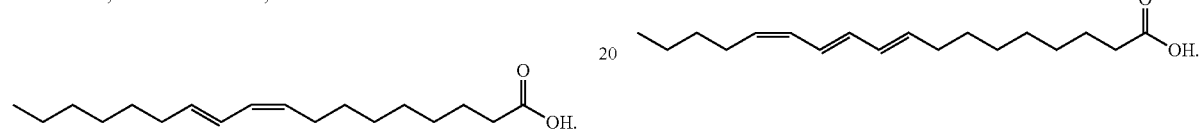

The term "punicic acid" or "(9Z,11E,13Z)-octadeca-9,11,13-trienoic acid," as used herein, refers to The term "rumelenic acid" or "(9E,11Z,15E)-octadeca-9,11,15-trienoic acid," as used herein, refers to The term "α-parinaric acid" or "(9Z,11E,13E,15Z)-octadeca-9,11,13,15-tetraenoic acid," as used herein, refers to The term "β-parinaric acid" or "(9E,11E,13E,15E)-octadeca-9,11,13,15-tetraenoic acid," as used herein, refers to The term "bosseopentaenoic acid" or "(5Z,8Z,10E,12E,14Z)-icosa-5,8,10,12,14-pentaenoic acid," as used herein, refers to

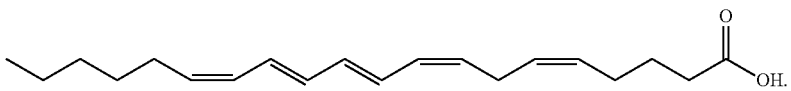

The term "pinolenic acid" or "(5Z,9Z,12Z)-octadeca-5,9,12-trienoic acid," as used herein, refers to

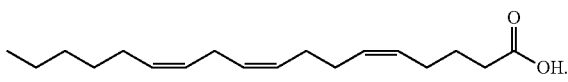 [SMILES: CCCCC/C=C\C/C=C\CC/C=C\CCCC(=O)O]

The term "podocarpic acid" or "(5Z,11Z,14Z)-icosa-5,11,14-trienoic acid," as used herein, refers to

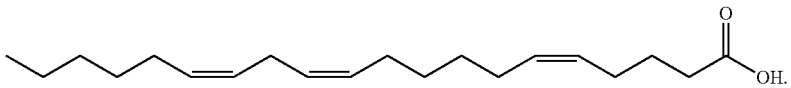

The term "propionic acid," as used herein, refers to $CH_3CH_2COOH$.
The term "butyric acid," as used herein, refers to $CH_3(CH_2)_2COOH$.
The term "valeric acid," as used herein, refers to $CH_3(CH_2)_3COOH$.
The term "caproic acid," as used herein, refers to $CH_3(CH_2)_4COOH$.
The term "enanthic acid," as used herein, refers to $CH_3(CH_2)_5COOH$.
The term "caprylic acid," as used herein, refers to $CH_3(CH_2)_6COOH$.
The term "pelargonic acid," as used herein, refers to $CH_3(CH_2)_7COOH$.
The term "capric acid," as used herein, refers to $CH_3(CH_2)_8COOH$.
The term "undecylic acid," as used herein, refers to $CH_3(CH_2)_9COOH$.
The term "lauric acid," as used herein, refers to $CH_3(CH_2)_{10}COOH$.
The term "tridecylic acid," as used herein, refers to $CH_3(CH_2)_{11}COOH$.
The term "myristic acid," as used herein, refers to $CH_3(CH_2)_{12}COOH$.
The term "pentadecylic acid," as used herein, refers to $CH_3(CH_2)_{13}COOH$.
The term "palmitic acid," as used herein, refers to $CH_3(CH_2)_{14}COOH$.
The term "margaric acid," as used herein, refers to $CH_3(CH_2)_{15}COOH$.
The term "stearic acid," as used herein, refers to $CH_3(CH_2)_{16}COOH$.
The term "nonadecylic acid," as used herein, refers to $CH_3(CH_2)_{17}COOH$.
The term "arachidic acid," as used herein, refers to $CH_3(CH_2)_{18}COOH$.
The term "heneicosylic acid," as used herein, refers to $CH_3(CH_2)_{19}COOH$.
The term "behenic acid," as used herein, refers to $CH_3(CH_2)_{20}COOH$.
The term "tricosylic acid," as used herein, refers to $CH_3(CH_2)_{21}COOH$.
The term "lignoceric acid," as used herein, refers to $CH_3(CH_2)_{22}COOH$.
The term "pentacosylic acid," as used herein, refers to $CH_3(CH_2)_{23}COOH$.
The term "cerotic acid," as used herein, refers to $CH_3(CH_2)_{24}COOH$.
The term "heptacosylic acid," as used herein, refers to $CH_3(CH_2)_{25}COOH$.
The term "montanic acid," as used herein, refers to $CH_3(CH_2)_{26}COOH$.
The term "nonacosylic acid," as used herein, refers to $CH_3(CH_2)_{27}COOH$.
The term "melissic acid," as used herein, refers to $CH_3(CH_2)_{28}COOH$.
The term "henatriacontylic acid," as used herein, refers to $CH_3(CH_2)_{29}COOH$.
The term "lacceroic acid," as used herein, refers to $CH_3(CH_2)_{30}COOH$.
The term "psyllic acid," as used herein, refers to $CH_3(CH_2)_{31}COOH$.
The term "geddic acid," as used herein, refers to $CH_3(CH_2)_{32}COOH$.
The term "ceroplastic acid," as used herein, refers to $CH_3(CH_2)_{33}COOH$.
The term "hexatriacontylic acid," as used herein, refers to $CH_3(CH_2)_{34}COOH$.

2. ALKOXYLATED SORBITAN ESTERS

Compounds of the invention include alkoxylated sorbitan esters including repeating units of propylene oxide and ethylene oxide. Compounds of the invention are useful as emulsion breakers, particularly for use in oil and gas industries.

Compounds of the invention exhibit multiple properties desirable of emulsion breakers (e.g., rapid water drop, good oil drying), such that the compounds can optionally be used in the absence of other materials to aid demulsification. Compounds of the invention exhibit favorable emulsion breaking properties compared to corresponding ethoxylated compounds lacking propylene oxide units, such as ethoxylated sorbitan esters sold under the trade name TWEEN®. Finally, compounds of the invention can be efficiently and economically produced and applied compared to conventional emulsion breakers.

In one aspect, alkoxylated sorbitan esters of the present invention have formula (I),

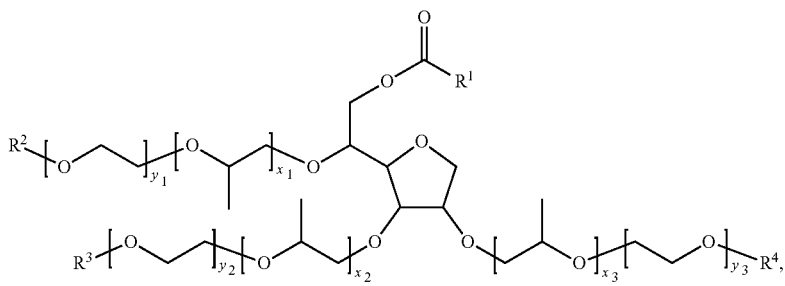

(I)

wherein,

R¹ is selected from the group consisting of alkyl, alkenyl, and alkynyl;

R², R³, and R⁴ are each independently selected from the group consisting of hydrogen, alkyl, alkenyl, alkynyl, aryl, cycloalkyl, heteroaryl, and heterocyclyl;

$x_1+x_2+x_3=x=0.2$ to 75; and $y_1+y_2+y_3=y=0$ to 250.

The term "x," as used in formula (I), refers to the molar equivalents of propylene oxide units present in the compound of formula (I) relative to the sorbitan ester. The term "y," as used in formula (I), refers to the molar equivalents of ethylene oxide units present in the compound of formula (I) relative to the sorbitan ester.

In certain embodiments, x ranges from 0.2 to 75, 0.2 to 50, 0.2 to 45, 0.2 to 30, 3 to 75, 3 to 50, 3 to 45, 3 to 30, 5 to 75, 5 to 50, 5 to 45, 5 to 30, 7 to 75, 7 to 50, 7 to 45, 7 to 30, 11 to 75, 11 to 50, 11 to 45, or 11 to 30. In certain embodiments, x is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, or about 75. In certain embodiments, x is about 2.8 to about 3.0, about 4.8 to about 5.0, about 7.3 to about 7.5, about 9.8 to about 10.0, about 11.1 to about 11.3, about 29.6 to about 29.8, or about 44.6 to about 44.9. In certain embodiments, x is about 2.90, about 2.91, about 2.92, about 2.93, about 2.94, about 2.95, about 2.96, about 2.97, about 2.98, about 2.99, or about 3.00. In certain embodiments, x is about 4.80, about 4.81, about 4.82, about 4.83, about 4.84, about 4.85, about 4.86, about 4.87, about 4.88, about 4.89, or about 4.90. In certain embodiments, x is about 7.30, about 7.31, about 7.32, about 7.33, about 7.34, about 7.35, about 7.36, about 7.37, about 7.38, about 7.39, or about 7.40. In certain embodiments, x is about 9.00, about 9.01, about 9.02, about 9.03, about 9.04, about 9.05, about 9.06, about 9.07, about 9.08, about 9.09, about 9.10, about 9.11, about 9.12, about 9.13, about 9.14, about 9.15, about 9.16, about 9.17, about 9.18, about 9.19, or about 9.20. In certain embodiments, x is about 11.15, about 11.16, about 11.17, about 11.18, about 11.19, about 11.20, about 11.21, about 11.22, about 11.23, about 11.24, about 11.25, about 11.26, about 11.27, about 11.28, about 11.29, about 11.30, about 11.31, about 11.32, about 11.33, about 11.34, or about 11.35. In certain embodiments, x is about 29.60, about 29.61, about 29.62, about 29.63, about 29.64, about 29.65, about 29.66, about 29.67, about 29.68, about 29.69, about 29.70, about 29.71, about 29.72, about 29.73, about 29.74, about 29.75, about 29.76, about 29.77, about 29.78, about 29.79, or about 29.80. In certain embodiments, x is about 44.60, about 44.61, about 44.62, about 44.63, about 44.64, about 44.65, about 44.66, about 44.67, about 44.68, about 44.69, about 44.70, about 44.71, about 44.72, about 44.73, about 44.74, about 44.75, about 44.76, about 44.77, about 44.78, about 44.79, about 44.78, about 44.79, about 44.80, about 44.81, about 44.82, about 44.83, about 44.84, about 44.85, about 44.86, about 44.87, about 44.88, 4 about 4.89, or about 44.90.

In certain embodiments, y ranges from 0 to 250, 0 to 200, 0 to 150, 0 to 100, 0 to 50, 0.1 to 250, 0.1 to 200, 0.1 to 150, 0.1 to 100, 0.1 to 50, 2 to 250, 2 to 200, 2 to 150, 2 to 100, or 2 to 50. In certain embodiments, y is 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250.

In certain embodiments, $R^1$ is substituted or unsubstituted alkyl. In certain embodiments, $R^1$ is unsubstituted alkyl selected from the group consisting of —$CH_2CH_3$; —$(CH_2)_2CH_3$; —$(CH_2)_3CH_3$; —$(CH_2)_4CH_3$; —$(CH_2)_5CH_3$; —$(CH_2)_6CH_3$; —$(CH_2)_7CH_3$; —$(CH_2)_8CH_3$; —$(CH_2)_9CH_3$; —$(CH_2)_{10}CH_3$; —$(CH_2)_{11}CH_3$; —$(CH_2)_{12}CH_3$; —$(CH_2)_{13}CH_3$; —$(CH_2)_{14}CH_3$; —$(CH_2)_{15}CH_3$; —$(CH_2)_{16}CH_3$; —$(CH_2)_{17}CH_3$; —$(CH_2)_{18}CH_3$; —$(CH_2)_{19}CH_3$; —$(CH_2)_{20}CH_3$; —$(CH_2)_{21}CH_3$; —$(CH_2)_{22}CH_3$; —$(CH_2)_{23}CH_3$; —$(CH_2)_{24}$—$CH_3$; —$(CH_2)_{25}CH_3$; —$(CH_2)_{26}CH_3$; —$(CH_2)_{27}CH_3$; —$(CH_2)_{28}CH_3$; —$(CH_2)_{29}CH_3$; —$(CH_2)_{30}CH_3$; —$(CH_2)_{31}CH_3$; —$(CH_2)_{32}CH_3$; —$(CH_2)_{33}CH_3$; and —$(CH_2)_{34}$—$CH_3$. In a preferred embodiment, $R^1$ is —$(CH_2)_{10}CH_3$.

In certain embodiments, —$C(O)R^1$ of formula (I) is derived from a saturated fatty acid. Suitable saturated fatty acids include, but are not limited to, propionic acid, butyric acid, valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, heneicosylic acid, behenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, and hexatriacontylic acid. In a preferred embodiment, —$C(O)R^1$ of formula (I) is derived from lauric acid.

In certain embodiments, $R^1$ is substituted or unsubstituted alkenyl. In certain embodiments, $R^1$ is unsubstituted alkenyl selected from the group consisting of —$(CH_2)_2CH=CHCH_2CH=CHCH_2CH=CHCH_2CH=CHCH_2CH=CH(CH_2)_4CH_3$; —$(CH_2)_2CH=CHCH_2CH=CHCH_2CH=CHCH_2CH=CHCH_2CH=CHCH_2CH_3$; —$(CH_2)_3CH=CHCH_2CH=CHCH_2CH=CH(CH_2)_7CH_3$; —$(CH_2)_3CH=CHCH_2CH_2CH=CHCH_2CH=CH(CH_2)_4CH_3$; —$(CH_2)_3CH=CH(CH_2)_4CH=CHCH_2CH=CH(CH_2)_4CH_3$; —$(CH_2)_3CH=CHCH_2CH=CHCH_2CH=CHCH_2CH=CH(CH_2)_4CH_3$; —$(CH_2)_3CH=CHCH_2CH=CHCH_2CH=CHCH_2CH=CHCH_2CH_3$; —$(CH_2)_3CH=CHCH=CHCH=CHCH=CH(CH_2)_4CH_3$; —$(CH_2)_4CH=CH(CH_2)_8CH_3$; —$(CH_2)_4CH=CHCH_2CH=CHCH_2CH=CH(CH_2)_4CH_3$; —$(CH_2)_4CH=CHCH_2CH=CHCH_2CH=CHCH_2CH=CHCH_2CH_3$; —$(CH_2)_4CH=CHCH_2CH=CHCH_2CH=CHCH_2CH=CHCH_2CH=CHCH_2CH_3$; —$(CH_2)_4CH=CHCH_2CH=CHCH_2CH=CHCH_2CH=CH(CH_2)_4CH_3$; —$(CH_2)_4CH=CHCH_2CH=CHCH_2CH=CHCH_2CH=CHCH_2CH=CHCH_2CH=CHCH_2CH_3$; —$(CH_2)_5CH=CHCH_2CH=CHCH_2CH=CHCH_2CH=CHCH_2CH_3$; —$(CH_2)_5CH=CHCH_2CH=CHCH_2CH=CHCH_2CH=CH(CH_2)_4CH_3$; —$(CH_2)_5CH=CHCH_2CH=CHCH_2CH=CHCH_2CH=CHCH_2CH=CHCH_2CH=CHCH_2CH_3$; —$(CH_2)_6CH=CHCH=CHCH=CH(CH_2)_4CH_3$; —$(CH_2)_6CH=CHCH_2CH=CHCH_2CH=CH(CH_2)_4CH_3$; —$(CH_2)_7CH=CH(CH_2)_3CH_3$; —$(CH_2)_7CH=CH(CH_2)_5CH_3$; —$(CH_2)_7CH=CH(CH_2)_7CH_3$; —$(CH_2)_7CH=CHCH=CHCH=CH(CH_2)_3CH_3$; —$(CH_2)_7CH=CHCH=CH(CH_2)_5CH_3$; —$(CH_2)_7CH=CHCH_2CH=CH(CH_2)_4CH_3$; —$(CH_2)_7CH=CHCH_2CH=CH(CH_2)_4CH_3$; —$(CH_2)_7CH=CHCH=CHCH_2CH_2CH=CHCH_2CH_3$; —$(CH_2)_7CH=CHCH=CHCH=CHCH=CHCH_2CH_3$; —$(CH_2)_7CH=CHCH_2CH=CHCH_2CH=CHCH_2CH=CH(CH_2)_4CH_3$; —$(CH_2)_7CH=CHCH_2CH=CHCH_2CH=CHCH_2$ $CH_3$; —$(CH_2)_7CH=CHCH_2CH=CHCH_2CH=CHCH_2CH_3$; —$(CH_2)_7CH=CHCH_2CH=CHCH_2CH=CHCH_2CH=CHCH_2CH_3$; —$(CH_2)_9CH=CH(CH_2)_5CH_3$; —$(CH_2)_9CH=CHCH_2CH=CH(CH_2)_4CH_3$; —$(CH_2)_9CH=CHCH_2CH=CHCH_2CH=CHCH_2CH_3$; —$(CH_2)_9CH=CH(CH_2)_7CH_3$; —$(CH_2)_{11}CH=CH(CH_2)_5CH_3$; —$(CH_2)_{11}CH=CH(CH_2)_7CH_3$; —$(CH_2)_{11}CH=CHCH_2CH=CH(CH_2)_4CH_3$; and —$(CH_2)_{13}CH=CH(CH_2)_7CH_3$. In a preferred embodiment, $R^1$ is —$(CH_2)_7CH=CH(CH_2)_7CH_3$.

In certain embodiments, —$C(O)R^1$ of formula (I) is derived from an unsaturated fatty acid. Suitable unsaturated fatty acids include, but are not limited to, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, hexadecatrienoic acid, stearidonic acid, eicosatrienoic acid, eicosatetraenoic acid, heneicosapentaenoic acid, clupanodonic acid, osbond acid, (9Z,12Z,15Z,18Z,21Z)-tetracosa-9,12,15,18,21-pentaenoic acid, nisinic acid, γ-linolenic acid, eicosadienoic acid, dihomo-γ-linolenic acid, docosadienoic acid, adrenic acid, tetracosatetraenoic acid, (6Z,9Z,12Z,15Z,18Z)-tetracosa-6,9,12,15,18-pentaenoic acid, (Z)-Eicos-11-enoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, and podocarpic acid. In a preferred embodiment, —$C(O)R^1$ of formula (I) is derived from oleic acid.

In certain embodiments, $R^2$, $R^3$, and $R^4$ are each independently hydrogen. Accordingly, alkoxylated sorbitan esters of the present invention may have formula (I-a),

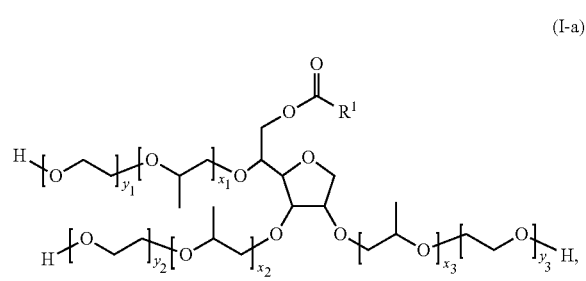

(I-a)

wherein $R^1$, $x_1$, $x_2$, $x_3$, $y_1$, $y_2$, and $y_3$ are as defined above.

In a preferred embodiment, $R^1$ is —$(CH_2)_{10}CH_3$, and $R^2$, $R^3$, and $R^4$ are each independently hydrogen. Accordingly, alkoxylated sorbitan esters of the present invention may have formula (I-b), (I-b)

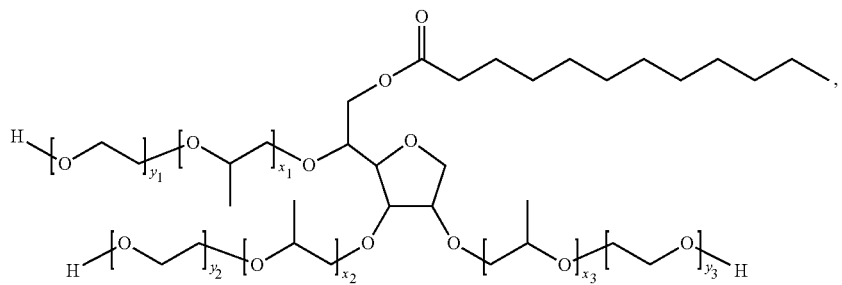

wherein $x_1$, $x_2$, $x_3$, $y_1$, $y_2$, and $y_3$ are as defined above.

In another preferred embodiment, alkoxylated sorbitan esters of the present invention may have formula (I-c), (I-c)

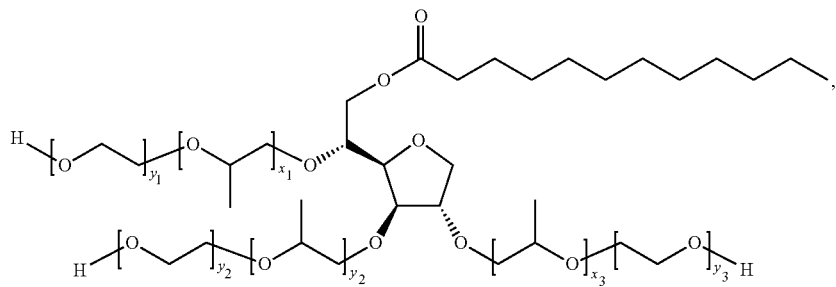

wherein $x_1$, $x_2$, $x_3$, $y_1$, $y_2$, and $y_3$ are as defined above.

In another preferred embodiment, $R^1$ is —$(CH_2)_7CH$=$CH(CH_2)_7CH_3$, and $R^2$, $R^3$, and $R^4$ are each independently hydrogen. Accordingly, alkoxylated sorbitan esters of the present invention may have formula (I-d), (I-d)

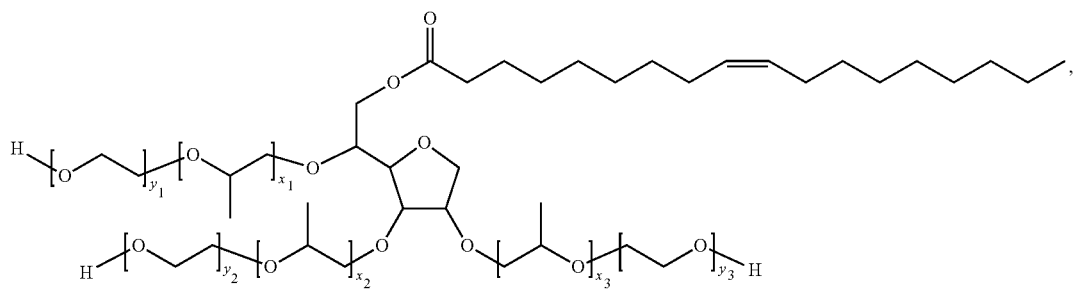

wherein $x_1$, $x_2$, $x_3$, $y_1$, $y_2$, and $y_3$ are as defined above.

In another preferred embodiment, alkoxylated sorbitan esters of the present invention may have formula (I-e),

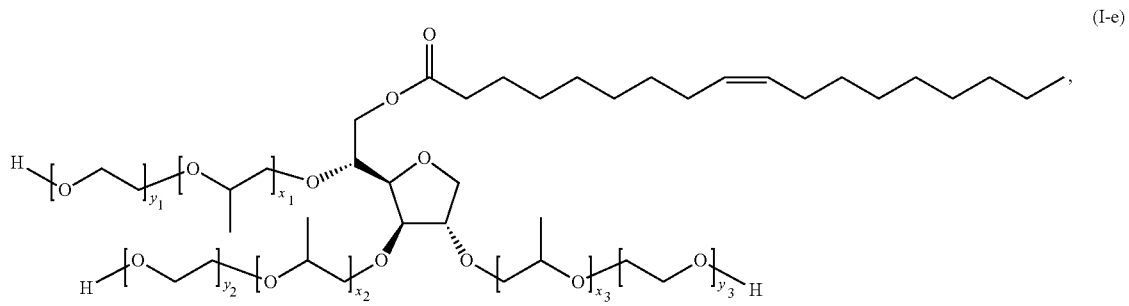

(I-e)

wherein $x_1$, $x_2$, $x_3$, $y_1$, $y_2$, and $y_3$ are as defined above.

In another aspect, alkoxylated sorbitan esters of the present invention have formula (II),

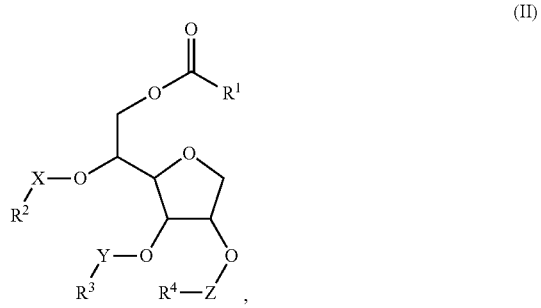

(II)

wherein $R^1$, $R^2$, $R^3$, and $R^4$ are as defined above, and

X, Y, and Z, are each independently selected from the group consisting of a bond, a chain consisting of repeating units of formula (a), a chain consisting of repeating units of formula (b), and a chain consisting of a mixture of repeating units of formula (a) and formula (b),

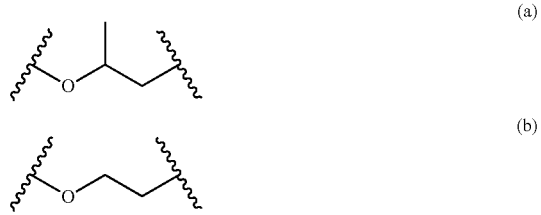

provided that at least one of X, Y, and Z is other than a bond; and provided that the compound of formula (II) comprises at least one repeating unit of formula (a) and optionally at least one repeating unit of formula (b).

In certain embodiments, the compound of formula (II) comprises 0.2 to 75, 0.2 to 50, 0.2 to 45, 0.2 to 30, 3 to 75, 3 to 50, 3 to 45, 3 to 30, 5 to 75, 5 to 50, 5 to 45, 5 to 30, 7 to 75, 7 to 50, 7 to 45, 7 to 30, 11 to 75, 11 to 50, 11 to 45, or 11 to 30 molar equivalents of repeating units of formula (a); and 0 to 250, 0 to 200, 0 to 150, 0 to 100, 0 to 50, 0.1 to 250, 0.1 to 200, 0.1 to 150, 0.1 to 100, 0.1 to 50, 2 to 250, 2 to 200, 2 to 150, 2 to 100, or 2 to 50 molar equivalents of repeating units of formula (b).

In certain embodiments, the compound of formula (II) comprises about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, or about 75 molar equivalents of repeating units of formula (a). In certain embodiments, the compound of formula (II) comprises about 2.8 to about 3.0, about 4.8 to about 5.0, about 7.3 to about 7.5, about 9.8 to about 10.0, about 11.1 to about 11.3, about 29.6 to about 29.8, or about 44.6 to about 44.9 molar equivalents of repeating units of formula (a). In certain embodiments, the compound of formula (II) comprises about 2.90, about 2.91, about 2.92, about 2.93, about 2.94, about 2.95, about 2.96, about 2.97, about 2.98, about 2.99, or about 3.00 molar equivalents of repeating units of formula (a). In certain embodiments, the compound of formula (II) comprises about 4.80, about 4.81, about 4.82, about 4.83, about 4.84, about 4.85, about 4.86, about 4.87, about 4.88, about 4.89, or about 4.90 molar equivalents of repeating units of formula (a). In certain embodiments, the compound of formula (II) comprises about 7.30, about 7.31, about 7.32, about 7.33, about 7.34, about 7.35, about 7.36, about 7.37, about 7.38, about 7.39, or about 7.40 molar equivalents of repeating units of formula (a). In certain embodiments, the compound of formula (II) comprises about 9.00, about 9.01, about 9.02, about 9.03, about 9.04, about 9.05, about 9.06, about 9.07, about 9.08, about 9.09, about 9.10, about 9.11, about 9.12, about 9.13, about 9.14, about 9.15, about 9.16, about 9.17, about 9.18, about 9.19, or about 9.20 molar equivalents of repeating units of formula (a). In certain embodiments, the compound of formula (II) comprises about 11.15, about 11.16, about 11.17, about 11.18, about 11.19, about 11.20, about 11.21, about 11.22, about 11.23, about 11.24, about 11.25, about 11.26, about 11.27, about 11.28, about 11.29, about 11.30, about 11.31, about 11.32, about 11.33, about 11.34, or about 11.35 molar equivalents of repeating units of formula (a). In certain embodiments, the compound of formula (II) comprises about 29.60, about 29.61, about 29.62, about 29.63, about 29.64, about 29.65, about 29.66, about 29.67, about 29.68, about 29.69, about 29.70, about 29.71, about 29.72, about 29.73, about 29.74, about 29.75, about 29.76, about 29.77, about 29.78, about 29.79, or about 29.80 molar equivalents of repeating units of formula (a). In certain embodiments, the compound of formula (II) comprises about 44.60, about 44.61, about 44.62, about 44.63, about 44.64, about 44.65, about 44.66, about 44.67, about 44.68, about 44.69, about 44.70, about 44.71, about 44.72, about 44.73, about 44.74, about 44.75, about 44.76, about 44.77, about 44.78, about 44.79, about 44.78, about 44.79, about 44.80, about 44.81, about 44.82, about 44.83, about 44.84, about 44.85, about 44.86, about 44.87, about 44.88, 4 about 4.89, or about 44.90 molar equivalents of repeating units of formula (a).

In certain embodiments, the compound of formula (II) comprises 0, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250 molar equivalents of repeating units of formula (b).

In certain embodiments, $R^1$ is —$(CH_2)_{10}CH_3$; $R^2$, $R^3$, and $R^4$ are each independently hydrogen; and the compound of formula (II) comprises: 0.2 to 75, 0.2 to 50, 0.2 to 45, 0.2 to 30, 3 to 75, 3 to 50, 3 to 45, 3 to 30, 5 to 75, 5 to 50, 5 to 45, 5 to 30, 7 to 75, 7 to 50, 7 to 45, 7 to 30, 11 to 75, 11 to 50, 11 to 45, or 11 to 30 molar equivalents of repeating units of formula (a); and 0 to 250, 0 to 200, 0 to 150, 0 to 100, 0 to 50, 0.1 to 250, 0.1 to 200, 0.1 to 150, 0.1 to 100, 0.1 to 50, 2 to 250, 2 to 200, 2 to 150, 2 to 100, or 2 to 50 molar equivalents of repeating units of formula (b). In other embodiments, $R^1$ is —$(CH_2)_7CH$=$CH(CH_2)_7CH_3$; $R^2$, $R^3$, and $R^4$ are each independently hydrogen; and the compound of formula (II) comprises: 0.2 to 75, 0.2 to 50, 0.2 to 45, 0.2 to 30, 3 to 75, 3 to 50, 3 to 45, 3 to 30, 5 to 75, 5 to 50, 5 to 45, 5 to 30, 7 to 75, 7 to 50, 7 to 45, 7 to 30, 11 to 75, 11 to 50, 11 to 45, or 11 to 30 molar equivalents of repeating units of formula (a); and 0 to 250, 0 to 200, 0 to 150, 0 to 100, 0 to 50, 0.1 to 250, 0.1 to 200, 0.1 to 150, 0.1 to 100, 0.1 to 50, 2 to 250, 2 to 200, 2 to 150, 2 to 100, or 2 to 50 molar equivalents of repeating units of formula (b).

In certain embodiments, each of X, Y, and Z is a chain consisting of a mixture of repeating units of formula (a) and formula (b). In other embodiments, one of X, Y, and Z is a bond, one of X, Y, and Z is a chain consisting of repeating units of formula (a), and one of X, Y, and Z is a chain consisting of repeating units of formula (b). In other embodiments, two of X, Y, and Z are a bond, and one of X, Y, and Z is a chain consisting of a mixture of repeating units of formula (a) and formula (b). In a preferred embodiment, each of X, Y, and Z is a chain consisting of a mixture of repeating units of formula (a) and formula (b), wherein the repeating units are arranged in block fashion by adding propylene oxide followed by ethylene oxide.

In a preferred embodiment, alkoxylated sorbitan esters of the invention may have formula (II-a),

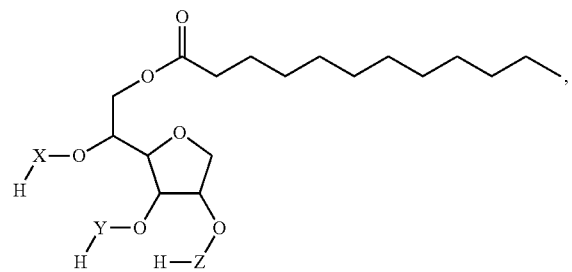

(II-a)

wherein X, Y, and Z are as defined above.

In another preferred embodiment, alkoxylated sorbitan esters of the invention may have formula (II-b),

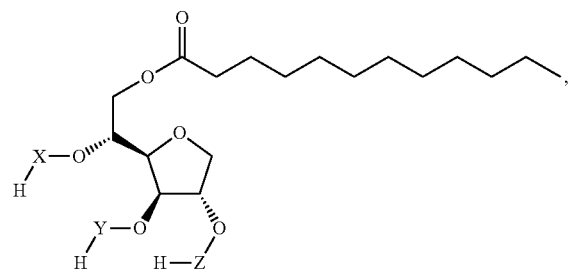

(II-b)

wherein X, Y, and Z are as defined above.

In another preferred embodiment, alkoxylated sorbitan esters of the invention may have formula (II-c), (II-c)

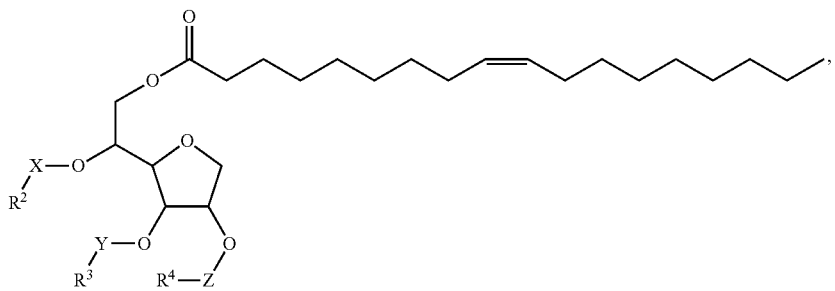

wherein X, Y, and Z are as defined above.

In another preferred embodiment, alkoxylated sorbitan esters of the invention may have formula (II-d), (II-d)

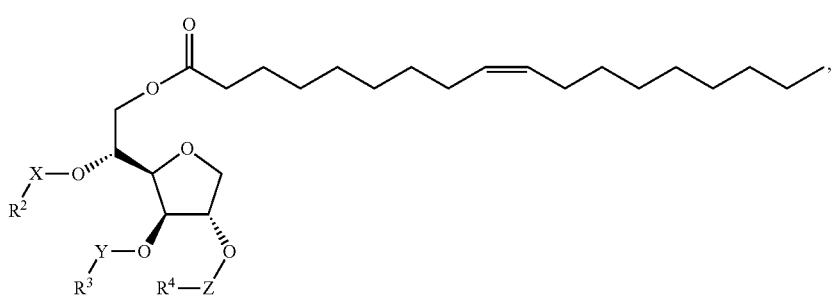

wherein X, Y, and Z are as defined above.

The alkoxylated sorbitan ester compounds of the invention may include propylene oxide and ethylene oxide repeating units arranged in any sequence. In certain embodiments, a chain extending from any of the respective sorbitan hydroxyl groups may be a homopolymer of two or more ethylene oxide or propylene oxide units. In certain embodiments, a chain extending from any of the respective sorbitan hydroxyl groups may be a copolymer of ethylene oxide and propylene oxide units. A copolymer chain of ethylene oxide and propylene oxide units may be an alternating copolymer chain, a periodic copolymer chain, a statistical copolymer chain, or a block copolymer chain. In a preferred embodiment, compounds of the invention include propylene oxide and ethylene oxide units arranged in block copolymer fashion, such that repeating propylene oxide units extend from one or more of the sorbitan hydroxyl groups, followed by ethylene oxide groups.

The compounds of the invention may contain asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds.

In certain embodiments, the alkoxylated sorbitan ester compounds and compositions of the invention may have a viscosity ranging from about 300 centipoise (cp) to 5000 cp. In certain embodiments, the alkoxylated sorbitan esters may be solids at room temperature.

In certain embodiments, the alkoxylated sorbitan ester compounds and compositions of the invention may have a weight average molecular weight ranging from about 300 Daltons to about 30,000 Daltons, or about 500 Daltons to about 20,000 Daltons. In certain embodiments, the alkoxylated sorbitan esters of the invention may have a weight average molecular weight of about 500 Daltons, about 1,000 Daltons, about 1,500 Daltons, about 2,000 Daltons, about 2,500 Daltons, about 3,000 Daltons, about 3,500 Daltons, about 4,000 Daltons, about 4,500 Daltons, about 5,000 Daltons, about 5,500 Daltons, about 6,000 Daltons, about 6,500 Daltons, about 7,000 Daltons, about 7,500 Daltons, about 8,000 Daltons, about 8,500 Daltons, about 9,000 Daltons, about 9,500 Daltons, about 10,000 Daltons, about 10,500 Daltons, about 11,000 Daltons, about 11,500 Daltons, about 12,000 Daltons, about 12,500 Daltons, about 13,000 Daltons, about 13,500 Daltons, about 14,000 Daltons, about 14,500 Daltons, about 15,000 Daltons, about 15,500 Daltons, about 16,000 Daltons, about 16,500 Daltons, about 17,000 Daltons, about 17,500 Daltons, about 18,000 Daltons, about 18,500 Daltons, about 19,000 Daltons, about 19,500 Daltons, about 20,000 Daltons, about 20,500 Daltons, about 21,000 Daltons, about 21,500 Daltons, about 22,000 Daltons, about 22,500 Daltons, about 23,000 Daltons, about 23,500 Daltons, about 24,000 Daltons, about 24,500 Daltons, or about 25,000 Daltons.

In certain embodiments, the alkoxylated sorbitan ester compounds and compositions of the invention may have a polydispersity (PD) of about 1.00, about 1.10, about 1.20, about 1.30, about 1.40, about 1.50, about 1.60, about 1.70, about 1.80, about 1.90, about 2.00, about 2.10, about 2.20, about 2.30, about 2.40, or about 2.50.

In certain embodiments, the alkoxylated sorbitan ester compounds and compositions of the invention may have an interfacial tension of about 8.0, about 8.5, about 9.0, about 9.5, about 10.0, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20.0, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, about 29.5, or about 30.0.

In certain embodiments, the alkoxylated sorbitan ester compounds and compositions of the invention may have an emulsion breaker performance of 90% or greater, 95% or greater, 100% or greater, 105% or greater, 110% or greater, 115% or greater, or 120% or greater as compared to an incumbent material, such as an alkylphenol formaldehyde resin alkoxylate, a polyalkylene glycol, or an organic sulfonate.

In certain embodiments, the alkoxylated sorbitan ester compounds and compositions of the invention may have a BS&W performance of less than or equal to 2.0 ml, less than or equal to 1.9 ml, less than or equal to 1.8 ml, less than or equal to 1.7 ml, less than or equal to 1.6 ml, less than or equal to 1.5 ml, less than or equal to 1.4 ml, less than or equal to 1.3 ml, less than or equal to 1.2 ml, less than or equal to 1.1 ml, less than or equal to 1.0 ml, less than or equal to 0.9 ml, less than or equal to 0.8 ml, less than or equal to 0.7 ml, less than or equal to 0.6 ml, less than or equal to 0.5 ml, less than or equal to 0.4 ml, less than or equal to 0.3 ml, less than or equal to 0.2 ml, or less than or equal to 0.1 ml.

In certain embodiments, the alkoxylated sorbitan ester compounds and compositions of the invention may drop greater than or equal to 10%, greater than or equal to 15%, greater than or equal to 20%, greater than or equal to 25%, greater than or equal to 30%, greater than or equal to 35%, greater than or equal to 40%, greater than or equal to 45%, greater than or equal to 50%, greater than or equal to 55%, greater than or equal to 60%, greater than or equal to 65%, greater than or equal to 70%, greater than or equal to 75%, greater than or equal to 80%, greater than or equal to 85%, greater than or equal to 90%, greater than or equal to 95%, or 100% water from a crude oil comprising a water/oil emulsion, and in particular, a water-in-oil emulsion.

3. SYNTHESIS OF ALKOXYLATED SORBITAN ESTERS

The compounds and compositions of the invention can be better understood in connection with the following synthetic schemes and methods which illustrate a means by which the compounds can be prepared.

Scheme 1

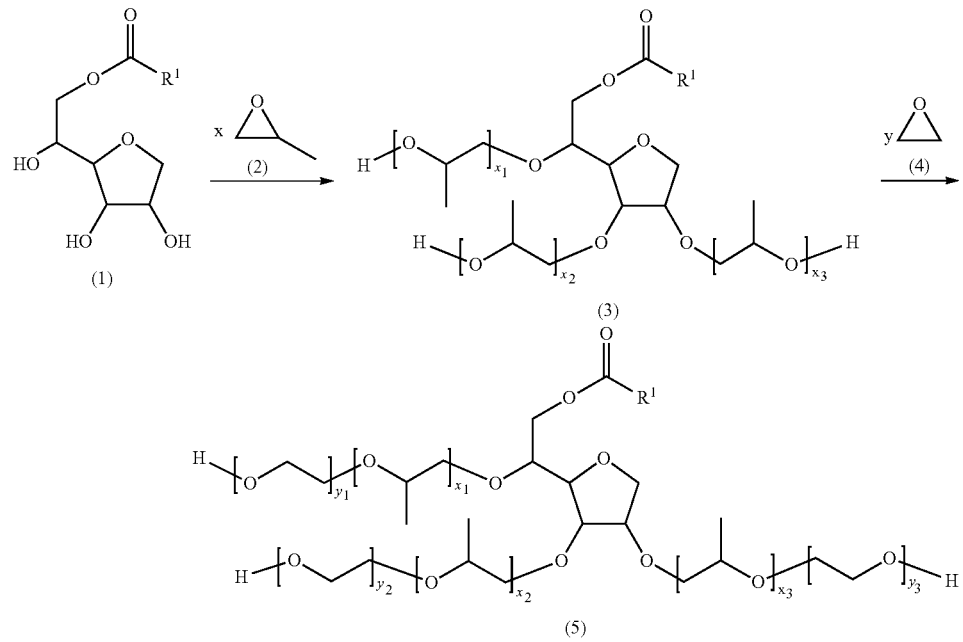

Alkoxylated sorbitan esters of formula (5) can be prepared as described in Scheme 1, wherein $R^1$, $x_1$, $x_2$, $x_3$, $y_1$, $y_2$, and $y_3$ are as defined above. Treatment of a sorbitan ester of formula (1) with x equivalents of propylene oxide of formula (2), preferably in the presence of a catalytic amount of a base, will provide a propoxylated sorbitan ester of formula (3). Suitable base catalysts include, but are not limited to, potassium hydroxide, and sodium hydroxide. Treatment of the propoxylated sorbitan ester of formula (3) with y equivalents of ethylene oxide will provide an alkoxylated sorbitan ester of formula (5).

Sorbitan esters of formula (1), such as sorbitan ester monooleate or sorbitan monolaurate, are commercially available from, for example, Lambent Technologies (Gurnee, Ill.), Croda (Edison, N.J.), or Sigma-Aldrich (Milwaukee, Wis.). Alternatively, sorbitan esters of formula (1) can be prepared by methods known to those skilled in the art. For example, a sorbitan ester of formula (1) can be prepared by conducting an esterification reaction between sorbitan and a fatty acid, preferably at an elevated temperature (e.g., 200° C.), under a flow of inert gas, and in the presence of an acidic or basic catalyst.

In an exemplary embodiment, an alkoxylated sorbitan ester of formula (5) can be prepared on a kilogram scale in a single reactor in, for example, a 5-gallon oxyalkylation reactor. The reactor can be charged with a sorbitan ester of formula (1). The sorbitan ester of formula (1) can be agitated and the reactor vented. A catalytic amount of a base, such as potassium hydroxide, can be added into the reactor. The reaction mixture can be mixed, and then heated to, for example, about 100° C. while purging with an inert gas, such as nitrogen. The purge rate can be adjusted as appropriate, for example, to 15 standard cubic feet per hour (scfh). The reactor may be dehydrated for an appropriate time, such as 30-45 minutes, to remove water. Preferably, the water content is at or below 0.1% before proceeding with the alkoxylation. Once dehydration is complete, the inert gas purge may be discontinued, the reactor vent closed, and the reactor padded with an inert atmosphere at, for example, 10 pounds per square inch (psi).

The reactor can be heated to about 130° C. to prepare for addition of a calculated quantity of propylene oxide of formula (2). Propylene oxide may be slowly charged into the reactor while maintaining the pressure below 50 psi. In certain embodiments, propylene oxide addition is preferably discontinued if the reactor pressure exceeds 50 psi. After addition of the propylene oxide, the reactor may be recycled down until a flat baseline is obtained (i.e., until system pressure stabilizes). Preferably, the oxide charge line is purged with inert gas prior to proceeding with ethylene oxide addition.

The reactor may next be heated to about 150° C. to prepare for addition of a calculated quantity of ethylene oxide of formula (4). Ethylene oxide may be added to the reactor while maintaining the reactor pressure below 50 psi. The temperature of the reactor may be maintained at about 150-160° C. by controlling the rate of ethylene oxide addition. After addition of the ethylene oxide, the reactor may be recycled down until a flat baseline is obtained. Upon completion of the reaction, the reactor may be cooled down to sampling temperature and the reaction mixture drummed out. Optionally, during the foregoing steps, aliquots may be sampled from the reactor and analyzed, such as for reaction product, propylene oxide content, ethylene oxide content, and/or water content by, for example, nuclear magnetic resonance (NMR) and/or gas chromatography (GC).

In certain embodiments, the alkoxylated sorbitan esters may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

4. PRODUCT BY PROCESS

In another aspect, alkoxylated sorbitan esters of the present invention are alkoxylated sorbitan esters prepared by treating a sorbitan ester with propylene oxide and ethylene oxide. In certain embodiments, the alkoxylated sorbitan esters are alkoxylated sorbitan esters prepared by treating a sorbitan ester with 0.2 to 75, 0.2 to 50, 0.2 to 45, 0.2 to 30, 3 to 75, 3 to 50, 3 to 45, 3 to 30, 5 to 75, 5 to 50, 5 to 45, 5 to 30, 7 to 75, 7 to 50, 7 to 45, 7 to 30, 11 to 75, 11 to 50, 11 to 45, or 11 to 30 molar equivalents of propylene oxide, followed by treatment with 0 to 250, 0 to 200, 0 to 150, 0 to 100, 0 to 50, 0.1 to 250, 0.1 to 200, 0.1 to 150, 0.1 to 100, 0.1 to 50, 2 to 250, 2 to 200, 2 to 150, 2 to 100, or 2 to 50 molar equivalents of ethylene oxide. In a preferred embodiment, the starting sorbitan ester is sorbitan monolaurate. In another preferred embodiment, the starting sorbitan ester is sorbitan monooleate. In another preferred embodiment, the compounds and compositions of the invention include compounds and compositions produced by processes as described above in Scheme 1.

In certain embodiments, the propylene oxide content and ethylene oxide content in the compounds and compositions produced by the processes disclosed herein can be represented in terms of weight percent, based on total weight of reactants. For example, a compound of formula (I) characterized as having 60% PO content and 30% EO content may mean a compound of formula (I), or composition of compounds of formula (I), derived from reaction of 10 wt % sorbitan ester starting material with 60 wt % propylene oxide, followed by reaction with 30 wt % ethylene oxide.

In certain embodiments, a compound of formula (I) comprises a propylene oxide content p of about 1-99 weight percent (wt %) propylene oxide; about 10-90 wt % propylene oxide; about 20-80 wt % propylene oxide; about 30-70 wt % propylene oxide; or about 40-60 wt % propylene oxide. In certain embodiments, a compound of formula (I) comprises a propylene oxide content p of about 5, about 10, about 15, about 20, about 25, about 30, about 35, about 40, about 45, about 50, about 55, about 60, about 65, about 70, about 75, about 80, about 85, about 90, or about 95 wt % propylene oxide.

In certain embodiments, a compound of formula (I) comprises an ethylene oxide content e of about 1-99 weight percent (wt %) ethylene oxide; about 10-90 wt % ethylene oxide; about 20-80 wt % ethylene oxide; about 30-70 wt % ethylene oxide; or about 40-60 wt % ethylene oxide. In certain embodiments, a compound of formula (I) comprises an ethylene oxide content e of about 5, about 10, about 15, about 20, about 25, about 30, about 35, about 40, about 45, about 50, about 55, about 60, about 65, about 70, about 75, about 80, about 85, about 90, or about 95 wt % ethylene oxide.

5. COMPOSITIONS

The compounds of the invention can be formulated into compositions useful for emulsion breaking applications. In certain embodiments, an emulsion breaking composition of the invention contains a pure composition of a compound of the invention. In other embodiments, an emulsion breaking composition of the invention contains a mixture of two or more structurally distinct compounds of the invention. For example, an emulsion breaking composition of the invention may comprise a mixture of compounds of formula (I), wherein the molar equivalents of propylene oxide and/or ethylene oxide units are varied between the two or more structurally distinct compounds, and/or wherein the $R^1$, $R^2$, $R^3$, and/or $R^4$ groups of formula (I) are varied between the two or more compounds.

In certain embodiments, an emulsion breaking composition of the invention comprises one or more compounds of the invention and one or more additives. Suitable additives include, but are not limited to, asphaltene inhibitors, paraffin inhibitors, corrosion inhibitors, scale inhibitors, emulsifiers, dispersants, emulsion breakers, hydrogen sulfide scavengers, gas hydrate inhibitors, pH modifiers, surfactants, and solvents.

Suitable asphaltene inhibitors include, but are not limited to, aliphatic sulphonic acids; alkyl aryl sulphonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable dispersants include, but are not limited to, dodecyl benzene sulfonate, oxyalkylated alkylphenols, and oxyalkylated alkylpnenolic resins.

Suitable corrosion inhibitors include, but are not limited to, amidoamines, quaternary amines, amides, and phosphate esters.

Suitable scale inhibitors include, but are not limited to, phosphates, phosphate esters, phosphoric acids, phosphonates, phosphonic acids, polyacrylamides, salts of acrylamido-methyl propane sulfonate/acrylic acid copolymer (AMPS/AA), phosphinated maleic copolymer (PHOS/MA), and salts of a polymaleic acid/acrylic acid/acrylamido-methyl propane sulfonate terpolymer (PMA/AMPS).

Suitable emulsifiers include, but are not limited to, salts of carboxylic acids, products of acylation reactions between carboxylic acids or carboxylic anhydrides and amines, and alkyl, acyl and amide derivatives of saccharides (alkyl-saccharide emulsifiers).

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate) and the triamine- and tetramine-polymethylene phosphonates with 2-4 methylene groups between each N atom, at least 2 of the numbers of methylene groups in each phosphonate being different. Other suitable dispersion agents include lignin or derivatives of lignin such as lignosulfonate and naphthalene sulfonic acid and derivatives.

Suitable emulsion breakers include, but are not limited to, dodecylbenzylsulfonic acid (DDBSA), the sodium salt of xylenesulfonic acid (NAXSA), anionic cationic and nonionic surfactants, resins such as phenolic and epoxide resins, alkoxylated alkylphenol-formaldehyde polymers, complex esters, alkoxylated phenols, alkoxylated alcohols, polyethylene or polypropylene glycols, and arylsulfonates.

Suitable hydrogen sulfide scavengers include, but are not limited to, oxidants (e.g., inorganic peroxides such as sodium peroxide, or chlorine dioxide), and aldehydes (e.g., of 1-10 carbons such as formaldehyde or glutaraldehyde or (meth) acrolein).

Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, NaCl salt, KCl salt, $CaCl_2$ salt, $MgCl_2$ salt, $NaBr_2$ salt, formate brines (e.g. potassium formate), polyols (such as glucose, sucrose, fructose, maltose, lactose, gluconate, monoethylene glycol, diethylene glycol, triethylene glycol, monopropylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate). Suitable kinetic hydrate inhibitors and anti-agglomerates include, but are not limited to, polymers and copolymers, polysaccharides (such as hydroxy-ethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include NaOH, KOH, $Ca(OH)_2$, CaO, $Na_2CO_3$, $KHCO_3$, $K_2CO_3$, $NaHCO_3$, MgO, and $Mg(OH)_2$.

Suitable surfactants include, but are not limited to, anionic surfactants, cationic surfactants, and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialky sulfosuccinates and sulfosuccinamates. Cationic surfactants include alkyl trimethyl quaternary ammonium salts, alkyl dimethyl benzyl quaternary ammonium salts, dialkyl dimethyl quaternary ammonium salts, and imidazolinium salts. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropripionates and amphodipropionates, and alkyliminodiproprionate.

Suitable solvents include, but are not limited to, isopropanol, methanol, ethanol, 2-ethylhexanol, heavy aromatic naphtha, toluene, ethylene glycol, ethylene glycol monobutyl ether (EGMBE), diethylene glycol monoethyl ether, and xylene. Representative polar solvents suitable for formulation with the compounds and compositions include water, brine, seawater, alcohols (including straight chain or branched aliphatic such as methanol, ethanol, propanol, isopropanol, butanol, 2-ethylhexanol, hexanol, octanol, decanol, 2-butoxyethanol, etc.), glycols and derivatives (ethylene glycol, 1,2-propylene glycol, 1,3-propylene glycol, ethylene glycol monobutyl ether, etc.), ketones (cyclohexanone, diisobutylketone), N-methylpyrrolidinone (NMP), N,N-dimethylformamide and the like. Representative of non-polar solvents suitable for formulation with the compounds and compositions include aliphatics such as pentane, hexane, cyclohexane, methylcyclohexane, heptane, decane, dodecane, diesel, and the like; aromatics such as toluene, xylene, heavy aromatic naphtha, fatty acid derivatives (acids, esters, amides), and the like. In certain embodiments, the solvent is an aromatic or mixture of aromatics. In certain embodiments, the solvent is a mixture of benzene, toluene, and xylene ("BTX"). In certain embodiments, the solvent is heavy aromatic naphtha ("HAN"). In certain embodiments, low-boiling solvents such as pentane, hexane and heptane are not utilized.

6. METHODS

The compounds and compositions of the invention, as described above, are particularly useful as emulsion breakers for use in the oil and gas industry, and in particular, to demulsify water-in-oil emulsions in various crude oil production and refinery processes. Accordingly, a method of the invention includes breaking an emulsion comprising oil and water, the method including adding to the emulsion an effective amount of a compound or composition of the invention. The compounds and compositions can be used for resolving a broad range of hydrocarbon emulsions encountered in crude oil production, refining and chemical processing. Specific examples include, but are not limited to, oilfield production emulsions, refinery desalting emulsions, refined fuel emulsions, and recovered oil emulsions (e.g., crude oil slop, used lubricant oils, and recovered oils in the steel and aluminum industries). In certain embodiments, a method of the invention includes breaking a crude oil emulsion comprising oil and water. The emulsion may be a water-in-oil emulsion. The emulsion may be a refinery desalting emulsion or a crude oil production emulsion.

In a refinery desalting process, the incoming crude may be deliberately mixed with wash water to remove dissolved salts and other contaminants. In certain embodiments, to extract water from the resulting water-in-crude oil emulsion, the emulsion can be admixed with an effective amount of a compound or composition of the invention, as described above.

In the process of resolving crude petroleum oil emulsions of the water-in-oil type, the compounds and compositions of the invention can be brought into contact with or caused to act upon the emulsion to be treated in any of the various methods now generally used in the petroleum industry to resolve or break crude petroleum oil emulsions with a chemical agent.

The compounds and compositions can be administered in several ways. The compounds and compositions can be used alone or blended with other emulsion breaker components. If used alone, the compounds and compositions may be dissolved in a suitable solvent or solvent mixture. In certain embodiments, an emulsion breaking solution comprising a compound or composition of the invention may include about 20 to about 60 percent actives (i.e., 80-40% solvent). In certain embodiments, an emulsion breaking solution may include about 40 to about 50 percent actives. Typical solvents include, but are not limited to, benzene, toluene, xylene, light or heavy aromatic naphtha, and kerosene. In certain embodiments, the compounds and compositions may be dissolved in aromatic naphtha for use as emulsion breakers. In certain embodiments, the compounds and compositions of the invention may be formulated to be water soluble.

In certain embodiments, the compounds and compositions of the invention are administered with co-solvents. Suitable co-solvents include, but are not limited to, alcohols ($C_3$ to $C_6$), glycol ethers, or polar aprotic solvents that are capable of dissolving both polar and non-polar materials. Typical co-solvents include, but are not limited to, isopropanol, 2-methyl-hexanol, 2-butoxyethanol, and dimethylformamide.

In certain embodiments, the compounds and compositions of the invention may be used alone or in blends with other emulsion breaker materials including, but not limited to, alkoxylated alkylphenol-formaldehyde polymers, complex esters, alkoxylated phenols, alkoxylated alcohols, polyethylene or polypropylene glycols and derivatives, and arylsulfonates.

In certain embodiments, the compounds and compositions of the invention may be used in combination with corrosion inhibitors, viscosity reducers and other chemical treatments used in crude oil production, refining and chemical processing.

With respect to resolving emulsions encountered in crude oil production, the compounds and compositions of the invention may be introduced into the crude oil emulsion by injecting beneath the surface into the oil well itself, by injecting into the crude oil at the well-head, or by injecting into the crude oil process stream at a point between the well-head and the final oil storage tank. The demulsifier composition may be injected continuously or in batch fashion. The injection may be accomplished using electric or gas pumps.

A treated crude oil emulsion may be allowed to stand in a quiescent state until the desired separation into distinct layers of water and oil results. Once separation into distinct layers of water and oil has been effected, various methods known in the art can be utilized for withdrawing the free water and separating crude oil.

In a typical process for demulsification of crude oil, a reservoir may be provided to hold the selected compound or compositions of the invention in either diluted or undiluted form adjacent to the point where the effluent crude petroleum oil leaves the well. For convenience, the reservoir may be connected to a proportioning pump capable of injecting the demulsifier into the fluids leaving the well, which then pass through a flow line into a settling tank. Generally, the well fluids pass into the settling tank at the bottom of the tank so that incoming fluids do not disturb stratification of the layers of crude petroleum oil and water that takes place during the course of demulsification.

In certain embodiments, the water-in-oil emulsion is a refinery desalting emulsion. A typical desalting process includes the use of pumps to move the incoming crude oil from storage tanks via piping through one or more heat exchangers. Wash water may be injected into the heated oil stream and the stream intimately mixed by an in-line mixing device. The emulsified stream may flow into an electrostatic desalter vessel where resolution and separation of the crude oil and water effluent occur. Injection of a compound or composition of the invention into the fluid stream can be carried out at various places along the path of the desalting process. Potential injection locations include prior to the crude oil storage tanks, on the outlet side of the crude oil storage tanks, upstream of the in-line mixer, into the wash water stream, and other potential locations.

The amount of the compounds and compositions used for emulsion breaking applications depends on the particular crude oil emulsion being treated. Bottle tests as described herein may be conducted in order to determine the optimum dose and formulation. With regard to specific emulsions, the following doses are typical, but may vary outside of the following ranges due to the specific characteristics of the emulsion:

Oilfield production: about 50 to about 500 ppm;
Desalting: about 1 to about 40 ppm;
Refined fuels: about 1 to about 50 ppm (pipeline); about 1 to about 250 ppm (static storage);
Recovered oils: about 250 to about 3000 ppm;
Diesel/finished gasoline: about 5 to about 75 ppm.

In certain embodiments, the compounds and compositions of the invention may be useful for other applications, such as resolving emulsions in butadiene, styrene, acrylic acid, and other hydrocarbon monomer process streams.

7. EXAMPLES

The foregoing may be better understood by reference to the following examples, which are presented for purposes of illustration and are not intended to limit the scope of the invention.

Viscosities (Vis) were determined on a Brookfield DV-II+ Pro kinematic viscometer at ambient temperature. Interfacial tension (IFT) measurements were determined on a Kruss Model K12 tensiometer at ambient temperature. The IFT tests were performed on 30 parts per million (ppm) solutions of alkoxylated sorbitan esters; the organic phase was 94% heptane and 6% toluene; and the aqueous phase was deionized water. Molecular weights (Mw) were determined via gel permeation chromatography/size exclusion chromatography (GPC/SEC) using a Shimadzu GPC equipped with two High Pressure Liquid Chromatography (HPLC) pumps (solvent delivery units), binary high pressure autoinjector, dual wavelength UV-visible detector, refractive index detector and data acquisition system. Precision Detectors were occasionally employed, which involved the use of a dual angle (15 and 90 degrees) laser light scattering module with an acquisition software and analysis package. The eluent used was HPLC grade tetrahydrofuran with 3% acetic acid.

Example 1

Alkoxylated Sorbitan Monooleate ($x_1+x_2+x_3=x=\sim 45$; $y_1+y_2+y_3=y=\sim 30$)

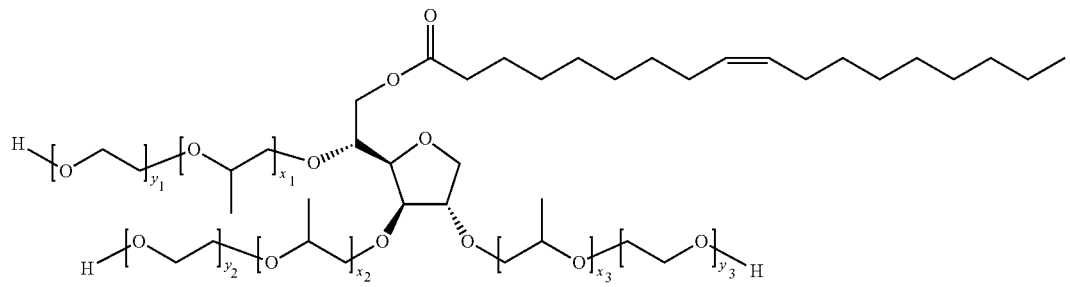

Synthesis of an alkoxylated sorbitan monooleate is described below. 2.6460 kilograms (kg) of sorbitan monooleate is charged to a 5-gallon oxyalkylation reactor. The sorbitan monooleate is agitated in the reactor and the reactor vented. 0.0540 kg of 45% aqueous potassium hydroxide is charged to the reactor. The mixture of sorbitan monooleate and potassium hydroxide base is mixed for 15 minutes. The reactor is heated to 100° C. while purging with nitrogen, at a purge rate of around 15 standard cubic feet per hour (scfh). The mixture is dehydrated for 30-45 to remove water. Venting and nitrogen purge is maintained until water content reaches 0.1% or less. After water content reaches 0.1% or less, nitrogen purge is discontinued, the reactor vent closed, and the reactor padded with 10 pounds per square inch (psi) of nitrogen atmosphere. The reactor is heated to 130° C. to prepare for propylene oxide addition. Once the temperature reaches 130° C., 16.2000 kg of propylene oxide is slowly added. The initial 0.5 kg of propylene oxide is slowly added into the reactor while maintaining the pressure below 50 psi. When all of the propylene oxide is added, the reactor is cycled down until a flat baseline is obtained. The oxide charge line (i.e., a small section between the nitrogen valve and the reactor) is purged with nitrogen to remove residual propylene oxide. The reactor is then heated to 150° C. to prepare for ethylene oxide addition. 8.1000 kg of ethylene oxide is added while maintaining the pressure in the reactor below 50 psi. The temperature is maintained at 150-160° C. by controlling the rate of ethylene oxide addition. When all of the ethylene oxide is added, the reactor is cycled down until a flat baseline is obtained. At the end of the reaction, the reactor is cooled down to sampling temperature and drummed out. The resulting product is analyzed for molecular weight, polydispersity, interfacial tension, and viscosity. Weight average molecular weight (Mw)=4399 Daltons; Number average molecular weight (Mn)=2876 Daltons; Z-average molecular weight (Mz)=6647 Daltons; Polydispersity=1.53; Interfacial tension=10.1 milliNewton/meter; Viscosity=1838 centipoise (cP).

Example 2

Alkoxylated Sorbitan Esters

Additional alkoxylated sorbitan esters were prepared according to the procedure of Example 1, and are summarized in Table 1, shown below. The table shows the molar amounts of starting sorbitan acceptor (SA), the molar amount of propylene oxide (PO), and the molar amount of ethylene oxide (EO) used to prepare the alkoxylated sorbitan esters. The table further shows molecular weight, interfacial tension, and viscosity data for the prepared compositions.

TABLE 1

| Ex | SA | mol SA mol | mol PO mol | mol EO mol | PO/SA mol ratio | EO/SA mol ratio | % PO % | % EO % | Mw Da | Mn Da | Mz Da | PD — | IFT | Vis cp |
|---|---|---|---|---|---|---|---|---|---|---|---|---|---|---|
| 1 | SO | 0.0236 | 1.0552 | 0.6475 | 44.71 | 27.44 | 61.19 | 28.49 | 4399 | 2876 | 6647 | 1.53 | 10.1 | 1838 |
| 2 | SO | 0.1249 | 0.3667 | 0.5672 | 2.936 | 4.541 | 21.27 | 24.96 | 1068 | 891 | 1235 | 1.199 | ND | 422 |
| 3 | SO | 0.05 | 0.1467 | 1.59 | 2.934 | 31.8 | 8.51 | 69.96 | 2430 | 1967 | 3115 | 1.235 | ND | solid |
| 4 | SO | 0.0334 | 0.0979 | 1.817 | 2.931 | 54.4 | 5.68 | 79.95 | 3854 | 2883 | 5549 | 1.337 | ND | solid |
| 5 | SO | 0.0893 | 0.8857 | 0.2293 | 9.918 | 2.568 | 51.37 | 10.09 | 1294 | 1134 | 1452 | 1.141 | 27.2 | 364 |
| 6 | SO | 0.0795 | 0.7884 | 0.3443 | 9.917 | 4.331 | 45.73 | 19.97 | 1438 | 1251 | 1628 | 1.149 | 12.5 | 401 |
| 7 | SO | 0.0596 | 0.5912 | 0.8939 | 9.919 | 15 | 34.29 | 39.99 | 1956 | 1617 | 3520 | 1.21 | 10.7 | 479 |
| 8 | SO | 0.0398 | 0.3945 | 1.3627 | 9.912 | 34.24 | 22.88 | 59.96 | 3096 | 2315 | 4511 | 1.337 | 17.1 | 598 |
| 9 | SO | 0.0298 | 0.2959 | 1.5902 | 9.93 | 53.36 | 17.16 | 69.97 | 4342 | 2995 | 7012 | 1.45 | ND | solid |
| 10 | SO | 0.0199 | 0.1972 | 1.8175 | 9.91 | 91.33 | 11.44 | 79.97 | 7400 | 4678 | 13228 | 1.582 | ND | solid |
| 11 | SO | 0.033 | 1.4755 | 0 | 44.71 | 0 | 85.58 | 0 | 2901 | 2294 | 3629 | 1.265 | 17.9 | 887 |
| 12 | SO | 0.0297 | 1.3284 | 0.2266 | 44.72 | 7.63 | 77.05 | 9.97 | 3200 | 2378 | 4203 | 1.346 | 14.6 | 597 |
| 13 | SO | 0.0264 | 1.1805 | 0.4543 | 44.72 | 17.21 | 68.47 | 19.99 | 3625 | 2572 | 4987 | 1.409 | 11.2 | 750 |
| 14 | SO | 0.025 | 1.1203 | 0.547 | 44.81 | 21.88 | 64.98 | 24.07 | 3960 | 2718 | 5616 | 1.457 | 10.5 | 1127 |
| 15 | SO | 0.0222 | 0.9941 | 0.7414 | 44.78 | 33.4 | 57.66 | 32.62 | 4840 | 3031 | 7395 | 1.597 | 10.7 | 4418 |
| 16 | SO | 0.0209 | 0.9345 | 0.8334 | 44.71 | 39.88 | 54.2 | 36.67 | 5477 | 3140 | 9268 | 1.744 | 11.8 | solid |
| 17 | SO | 0.0181 | 0.8097 | 1.0257 | 44.73 | 56.67 | 46.96 | 45.13 | 6684 | 3600 | 12403 | 1.857 | 15.8 | solid |
| 18 | SO | 0.0151 | 0.6771 | 1.23 | 44.84 | 81.46 | 39.27 | 54.12 | 8546 | 4409 | 1554 | 1.938 | 18.9 | solid |
| 19 | SO | 0.0121 | 0.5421 | 1.438 | 44.8 | 118.8 | 31.44 | 63.27 | 11915 | 5698 | 12265 | 2.091 | 19.4 | solid |
| 20 | SO | 0.0087 | 0.388 | 1.6752 | 44.6 | 192.6 | 22.5 | 73.71 | 19435 | 8709 | 37329 | 2.232 | — | solid |
| 21 | SL | 0.1673 | 1.236 | 0.2305 | 7.388 | 1.378 | 17.98 | 16.99 | 576 | 432 | 705 | 1.333 | 19.7 | 1294 |
| 22 | SL | 0.158 | 1.1672 | 0.3445 | 7.387 | 2.18 | 16.98 | 15.16 | 609 | 461 | 742 | 1.321 | ND | 1012 |
| 23 | SL | 0.1477 | 1.0914 | 0.4698 | 7.389 | 3.181 | 15.88 | 20.67 | 641 | 484 | 783 | 1.324 | 17.1 | 868 |
| 24 | SL | 0.1391 | 1.0278 | 0.5748 | 7.389 | 4.132 | 14.95 | 25.29 | 678 | 509 | 835 | 1.332 | ND | 776 |
| 25 | SL | 0.1297 | 0.9584 | 0.6893 | 7.389 | 5.315 | 13.94 | 30.33 | 712 | 540 | 865 | 1.319 | 15.1 | 648 |
| 26 | SL | 0.1203 | 0.8891 | 0.8039 | 7.391 | 6.682 | 12.93 | 35.37 | 758 | 571 | 928 | 1.327 | ND | 573 |
| 27 | SL | 0.1109 | 0.8195 | 0.9189 | 7.39 | 8.286 | 11.92 | 40.43 | 810 | 634 | 971 | 1.278 | 13.8 | 516 |
| 28 | SL | 0.0922 | 0.681 | 1.1477 | 7.386 | 12.45 | 9.9 | 50.5 | 937 | 771 | 1097 | 1.215 | 11.3 | 462 |
| 29 | SL | 0.0735 | 0.5434 | 1.3748 | 7.393 | 18.7 | 7.91 | 60.49 | 1120 | 962 | 1271 | 1.164 | 12.4 | 437 |
| 30 | SL | 0.0548 | 0.4048 | 1.6039 | 7.387 | 29.27 | 5.89 | 70.57 | 1410 | 1202 | 1616 | 1.173 | 15.7 | 472 |
| 31 | SL | 0.0362 | 0.2678 | 1.8305 | 7.398 | 50.69 | 3.89 | 80.54 | 2033 | 1813 | 2242 | 1.21 | ND | solid |
| 32 | SL | 0.1203 | 0.5891 | 0.32 | 4.897 | 2.66 | 34.17 | 14.08 | 716 | 608 | 811 | 1.178 | ND | 690 |
| 33 | SL | 0.1137 | 0.5566 | 0.428 | 4.895 | 3.764 | 32.28 | 18.83 | 754 | 632 | 861 | 1.193 | 16.5 | 601 |
| 34 | SL | 0.107 | 0.5241 | 0.5355 | 4.898 | 5.005 | 30.4 | 23.56 | 791 | 658 | 910 | 1.202 | ND | 548 |
| 35 | SL | 0.1003 | 0.4912 | 0.6445 | 4.897 | 6.426 | 28.49 | 28.36 | 831 | 700 | 947 | 1.187 | 14 | 503 |
| 36 | SL | 0.0935 | 0.4579 | 0.755 | 4.897 | 8.075 | 26.56 | 33.22 | 867 | 733 | 982 | 1.183 | ND | 464 |
| 37 | SL | 0.0868 | 0.4248 | 0.8643 | 4.894 | 9.957 | 24.64 | 38.03 | 922 | 785 | 1042 | 1.175 | 10.9 | 454 |
| 38 | SL | 0.0923 | 1.0388 | 0 | 11.25 | 0 | 60.25 | 0 | 946 | 811 | 1078 | 1.166 | 21.4 | 548 |
| 39 | SL | 0.0877 | 0.9867 | 0.1136 | 11.25 | 1.295 | 57.23 | 5 | 910 | 781 | 1022 | 1.165 | 19.2 | 490 |
| 40 | SL | 0.083 | 0.9344 | 0.2282 | 11.26 | 2.749 | 54.19 | 10.04 | 958 | 828 | 1074 | 1.157 | 18 | 474 |
| 41 | SL | 0.0691 | 0.7772 | 0.5718 | 11.25 | 8.275 | 45.08 | 25.16 | 1127 | 974 | 1273 | 1.157 | 12.8 | 412 |
| 42 | SL | 0.0367 | 0.4129 | 1.3693 | 11.25 | 37.31 | 23.95 | 60.25 | 1942 | 1698 | 2189 | 1.144 | 15 | 810 |
| 43 | SL | 0.0275 | 0.309 | 1.5968 | 11.24 | 58.07 | 17.92 | 70.26 | 2470 | 2159 | 2774 | 1.144 | 17.6 | solid |
| 44 | SO | 0.0418 | 1.2409 | 0.2273 | 29.69 | 5.438 | 71.91 | 10 | 2594 | 2268 | 2929 | 1.144 | 12.7 | 538 |
| 45 | SO | 0.0372 | 1.1029 | 0.4534 | 29.65 | 12.19 | 63.97 | 19.95 | 2965 | 2559 | 3425 | 1.159 | 8.6 | 592 |
| 46 | SO | 0.0464 | 1.3776 | 0 | 29.69 | 0 | 79.9 | 0 | 2345 | 2149 | 2535 | 1.091 | 16.6 | 561 |
| 47 | SO | 0.0348 | 1.0331 | 0.5686 | 29.69 | 16.34 | 59.92 | 25.02 | 2972 | 2515 | 3455 | 1.182 | ND | 1101 |
| 48 | SO | 0.0325 | 0.9643 | 0.6818 | 29.67 | 20.98 | 55.93 | 30 | 3176 | 2588 | 3803 | 1.227 | 7.2 | 1192 |
| 49 | SO | 0.0302 | 0.8955 | 0.7952 | 29.65 | 26.33 | 51.94 | 34.99 | 3444 | 2566 | 4394 | 1.342 | ND | 1292 |
| 50 | SO | 0.0279 | 0.8271 | 0.9082 | 29.65 | 32.55 | 47.97 | 39.96 | 3677 | 2793 | 4589 | 1.317 | 8.3 | 1268 |
| 51 | SO | 0.0256 | 0.7595 | 1.0191 | 29.67 | 39.81 | 44.05 | 44.87 | 3962 | 2965 | 4980 | 1.336 | ND | solid |
| 52 | SO | 0.0233 | 0.6919 | 1.1311 | 29.7 | 48.55 | 40.13 | 49.77 | 4376 | 3269 | 5569 | 1.339 | 13.3 | solid |
| 53 | SO | 0.0188 | 0.5579 | 1.3523 | 29.68 | 71.93 | 32.36 | 59.5 | 5368 | 3929 | 6983 | 1.368 | 17.8 | solid |
| 54 | SO | 0.0143 | 0.4247 | 1.5723 | 29.7 | 109.95 | 24.63 | 69.18 | 7040 | ND | ND | ND | ND | solid |
| 55 | SO | 0.0098 | 0.2917 | 1.7916 | 29.77 | 182.8 | 16.92 | 78.83 | 10105 | 6956 | 13961 | 1.453 | ND | solid |

Ex = Example No.; SA = sorbitan acceptor; SO = sorbitan monooleate; SL = sorbitan monolaurate; PO = propylene oxide; EO = ethylene oxide; Mw = weight average molecular weight; Mn = number average molecular weight; Mz = z-average molecular weight; PD = polydispersity; IFT = interfacial tension; Vis = viscosity.

Example 3

Testing of Emulsion Breakers for Oilfield Applications

The alkoxylated sorbitan compounds and compositions disclosed in Table 1 were evaluated for performance in oilfield applications, as described in Tables 2-4. The compounds and compositions were evaluated in Oilfield 1 (LA), Oilfield 2 (WY), Oilfield 3 (CA), Oilfield 4 (LA), Oilfield 5 (Canada), Oilfield 6 (LA), and Oilfield 7 (CA), using various oilfield emulsion performance tests such as water drop, basic sediment & water (BS&W), and the absolute test (a combined analysis of water drop and BS&W).

Oilfield emulsion breaker tests are performed using a typical bottle test procedure that is well known to those skilled in the art. A fresh emulsion sample is collected from a field site. The site selected provides a sample that is free from emulsion breaker additives. Free water is removed and the remaining emulsion is transferred into graduated bottles. Bottles are placed in a bath at field system temperature, such as downhole temperature. Test chemicals are added and contents of the bottle are mixed with hand agitation (e.g., 100 shakes by hand) or a mechanical shaker (e.g., 2 minutes on high using a mechanical shaker). The bottles are again placed in a bath at field system temperature, preferably the temperature used in the field separation equipment. The length of the test is preferably adjusted to match the residence time of the fluids in the field separation equipment. Water separation (water drop) is measured and is recorded at timed intervals (e.g., at 3, 15, 30, 45, and 60 minutes, although additional or fewer points may be used). This series of measurements indicates the ability of the test chemical to assist in water coalescence from the emulsion.

At the conclusion of the water drop test, a volume (e.g., 6-7 ml) of thief sample is withdrawn from the oil layer using a pipet. Preferably, oil is sampled from above the oil-water interface, more preferably 15 ml above the oil-water interface. The thief sample is transferred to a centrifuge tube and blended with a hydrocarbon solvent (e.g., xylenes, stoddard solvent, or varsol). Preferably, the centrifuge tube is filled with 50% hydrocarbon solvent/50% thief sample by volume. The centrifuge tube is then centrifuged, preferably at 2000-5000 revolutions per minute for 4-5 minutes. The amount of water in the thief sample is determined from the water collected in the bottom of the centrifuge tube. This measurement indicates the ability of the test chemical to provide dry crude oil.

Finally, the dropped free water layer is separated from the original test bottle. The remaining crude oil and emulsion is thoroughly mixed to form a composite (the BS&W for the resolved oil phase). A composite sample is transferred to a centrifuge tube, blended with a hydrocarbon solvent and emulsion breaker chemical, and centrifuged. The amount of water and solids in the composite sample is determined from the quantity measured in the bottom of the centrifuge tube. This measurement indicates the ability of the test chemical to break interface emulsion.

A. Water Drop

Table 2 shows water drop for exemplary alkoxylated sorbitan esters. The alkoxylated sorbitan ester compositions were applied in three different oilfields and evaluated for water drop according to the procedure described above. The table shows that the alkoxylated sorbitan esters outperformed the incumbent material in each test with respect to the final amount of water drop.

TABLE 2

| Oilfield 1 | | Oilfield 2 | | Oilfield 3 | |
|---|---|---|---|---|---|
| Example No. | Water Drop (ml) | Example No. | Water Drop (ml) | Example No. | Water Drop (ml) |
| Incumbent | 16 | Incumbent | 51 | Incumbent | 40 |
| 2 | 22 | 12 | 52 | 51 | 42 |
| 3 | 20 | 13 | 52 | 52 | 45 |
| 4 | 20 | 14 | 53 | 53 | 45 |
| 9 | 25 | 1 | 52 | 54 | 43 |
| 10 | 20 | | | 55 | 43 |

B. BS&W

Table 3 shows BS&W performance for exemplary alkoxylated sorbitan esters disclosed in Table 1. The alkoxylated sorbitan ester compositions were applied in three different oilfields and evaluated for BS&W according to the procedure described above. The table shows that the alkoxylated sorbitan esters outperformed the incumbent material in each test with respect to the amount of BS&W.

TABLE 3

| Oilfield 1 | | Oilfield 4 | | Oilfield 5 | |
|---|---|---|---|---|---|
| Example No. | BS&W (ml) | Example No. | BS&W (ml) | Example No. | BS&W (ml) |
| Incumbent | 0.5 | Incumbent | 1.5 | Incumbent | 6 |
| 31 | 0.3 | 48 | 1.2 | 41 | 1 |
| 32 | 0.2 | 49 | 1.2 | 37 | 2 |
| 33 | 0.4 | Incumbent | 1.2 | Incumbent | 3.2 |
| 34 | 0.2 | 11 | 0.4 | 1 | 3 |
| 35 | 0.4 | 12 | 0.4 | 15 | 3.2 |
| Incumbent | 0.4 | 13 | 0.5 | | |
| 38 | 0.3 | 14 | 0.2 | | |
| 39 | 0.2 | 1 | 0.6 | | |
| 40 | 0.4 | | | | |
| 42 | 0.4 | | | | |
| 43 | 0.4 | | | | |
| Incumbent | 1.1 | | | | |
| 21 | 0.9 | | | | |
| 22 | 0.6 | | | | |
| 23 | 0.5 | | | | |
| 24 | 0.4 | | | | |
| 25 | 0.4 | | | | |
| 26 | 0.4 | | | | |
| 27 | 0.4 | | | | |
| 28 | 0.4 | | | | |
| 29 | 0.4 | | | | |
| Incumbent | 0.7 | | | | |
| 46 | 0.4 | | | | |
| 47 | 0.4 | | | | |
| 48 | 0.4 | | | | |
| 49 | 0.4 | | | | |
| 50 | 0.4 | | | | |
| 51 | 0.4 | | | | |
| 52 | 0.4 | | | | |
| 53 | 0.3 | | | | |
| 54 | 0.4 | | | | |
| 55 | 0.2 | | | | |

C. Absolute

Table 4 shows exemplary alkoxylated sorbitan esters from Table 1 where either the water drop exceeded 90% of a currently available emulsion breaker (i.e., an incumbent) or the BS&W term was found to be less than 2. Emulsion breakers that met either one or both of these criteria were considered to be good performers.

TABLE 4

| Oilfield 1 | | | Oilfield 3 | | | Oilfield 4 | | |
|---|---|---|---|---|---|---|---|---|
| Example No. | WD % of incumbent | BS&W (ml) | Example No. | WD % of incumbent | BS&W (ml) | Example No. | WD % of incumbent | BS&W (ml) |
| 13 | | 0.5 | 13 | 100 | | 13 | 100 | 1.6 |
| 14 | | 0.4 | 14 | 100 | | 14 | 97 | 0.8 |
| 1 | | 0.4 | 1 | 100 | | 1 | 97 | 1.6 |
| 15 | | 0.4 | 15 | 100 | 1.4 | 15 | 100 | 1.2 |
| 16 | | 0.6 | 16 | 100 | 0.6 | 16 | 97 | 1.5 |
| 17 | | 1 | 17 | 94 | | 17 | 85 | 2 |
| 18 | | 1.2 | 18 | 100 | | 18 | 97 | |
| 19 | | 0.5 | 19 | 100 | | 19 | 90 | |
| 20 | | 0.6 | 20 | 94 | | 20 | 85 | |

TABLE 4-continued

|  |  |  |  |  |
|---|---|---|---|---|
| 1 |  | 1.8 | 16 | 84 | 1.6 |
| 15 |  | 1.4 |  |  |
| 16 |  | 1.2 | 16 | 100 |
| 17 |  | 0.9 |  |  |
| 18 |  | 1.6 |  |  |
| 19 |  | 1.9 |  |  |

| Oilfield 5 | | | Oilfield 6 | | | Oilfield 7 | | |
|---|---|---|---|---|---|---|---|---|
| Example No. | WD % of incumbent | BS&W (ml) | Example No. | WD % of incumbent | BS&W (ml) | Example No. | WD % of incumbent | BS&W (ml) |
| 18 | 111 |  | 12 | 102 | 0.4 | 18 |  | 1.8 |
|  |  |  | 13 | 102 | 0.5 |  |  |  |
|  |  |  | 14 | 104 | 0.2 |  |  |  |
|  |  |  | 1 | 102 | 0.6 |  |  |  |
|  |  |  | 14 | 94 |  |  |  |  |
|  |  |  | 15 | 94 |  |  |  |  |
|  |  |  | 14 | 92 |  |  |  |  |
|  |  |  | 1 | 98 |  |  |  |  |
|  |  |  | 15 | 98 |  |  |  |  |
|  |  |  | 16 | 94 |  |  |  |  |
|  |  |  | 17 | 92 |  |  |  |  |
|  |  |  | 14 | 98 |  |  |  |  |
|  |  |  | 15 | 96 |  |  |  |  |

Example 4

Comparison to Ethoxylated Sorbitans

Commercially available sorbitan ethoxylates, TWEENS®, were evaluated for water drop and BS&W. Table 5 and 6 show that the evaluated sorbitan ethoxylates provided either a small percentage of water drop and/or a large amount of BS&W compared to the compounds and compositions disclosed herein.

TABLE 5

| Sample No. | Tween® | Name | wt % EO |
|---|---|---|---|
| A | 20 | sorbitan monolaurate ethoxylate | 72 |
| B | 21 | sorbitan monolaurate ethoxylate | 34 |
| C | 40 | sorbitan monopalmitate ethoxylate | 69 |
| D | 60 | sorbitan monostearate ethoxylate | 67 |
| F | 61 | sorbitan monostearate ethoxylate | 29 |
| G | 65 | sorbitan tristearate ethoxylate | 48 |
| H | 80 | sorbitan monooleate ethoxylate | 67 |
| J | 85 | sorbitan trioleate ethoxylate | 48 |
| K | 81N | sorbitan monooleate ethoxylate | 34 |

TABLE 6

| Field A (76° C., 300 ppm dose) | | | | Field B (100° F., 100 ppm dose) | | | | Field C (196° F., 400 ppm dose) | | | |
|---|---|---|---|---|---|---|---|---|---|---|---|
| | TG | | WD % of | | TG | | WD % of | | TG | | WD % of |
| Chem. | BS | W | Inc. | Chem. | BS | W | Inc. | Chem. | BS | W | Inc. |
| Incumbent | 3.2 | 0 | — | Incumbent | 0.1 | 0 | — | Incumbent | 0.5 | 1.5 | — |
| Blank | 33 | 1 | 47 | Blank |  |  | 36 | Blank | 20 | 11 | — |
| A | 10 | 18 | 47 | A | 46 | 0 | 40 | A | 38 | 12 | 21 |
| B | 7 | 11 | 27 | B | 52 | 0 | 36 | B | 44 | 9 | 10 |
| C | 13 | 15 | 40 | C | 48 | 0 | 44 | C | 30 | 20 | 19 |
| D | 12 | 14 | 53 | D | 52 | 0 | 42 | D | 28 | 18 | 19 |
| F | 18 | 8 | 23 | F | 54 | 0 | 36 | F | 24 | 20 | 12 |
| G | 16 | 8 | 63 | G | 54 | 0 | 40 | G | 12 | 34 | 12 |
| H | 14 | 14 | 60 | H | 44 | 0 | 48 | H | 28 | 20 | 24 |
| J | 14 | 8 | 50 | J | 52 | 0 | 38 | J | 24 | 24 | 21 |
| K | 21 | 8 | 17 | K | 54 | 0 | 36 | K | 40 | 14 | 10 |

| Field D (133° F., 100 ppm dose) | | | | Field F (120° F., 300 ppm dose) | | | |
|---|---|---|---|---|---|---|---|
| | TG | | WD % of | | TG | | WD % of |
| Chem. | BS | W | Inc. | Chem. | BS | W | Inc. |
| Incumbent | 0.2 | 0.1 | — | Incumbent | 0.5 | 0.7 | — |
| Blank | 31 | 0 | 66 |  |  |  |  |
| A | 14.5 | 9.5 | 76 | A | 0.8 | 1.2 | 9 |
| B | 13 | 11 | 75 | B | 1.2 | 2.4 | 36 |
| C | 15 | 7 | 73 | C | 0.7 | 1.2 | 9 |

TABLE 6-continued

| | | | | | | | |
|---|---|---|---|---|---|---|---|
| D | 4 | 16 | 75 | D | 0.8 | 1.2 | 0 |
| F | 20.4 | 5.8 | 73 | F | 3.2 | 5.2 | 14 |
| G | 15 | 4.8 | 81 | G | 0.5 | 1 | 9 |
| H | 14 | 8 | 78 | H | 0.6 | 1 | 9 |
| J | 8 | 10 | 81 | J | 0.5 | 0.8 | 14 |
| K | 11 | 13 | 73 | K | 2.8 | 4.6 | 9 |

Chem. = chemical; TG = Thief Grindout; Inc. = incumbent; WD % of Inc. = water drop percent of incumbent.

Table 7 shows a direct comparison between alkoxylated sorbitan esters disclosed herein and commercially available sorbitan ethoxylates. The data shows that the compounds and compositions of the invention exhibit superior water drop and BS&W.

TABLE 7

Field G (165° F., 200 ppm dose)

| Chem./Ex. No. | TG | | WD % of Inc. |
|---|---|---|---|
| | BS | W | |
| Incumbent | 1.1 | 1.1 | — |
| A | 18 | 19 | 32 |
| B | 30 | 32 | 13 |
| C | 28 | 28 | 26 |
| 27 | 10 | 10 | 76 |
| 28 | 19 | 19 | 61 |
| 29 | 18 | 18 | 61 |
| 30 | 16 | 16 | 55 |
| 31 | 8 | 8 | 71 |
| 42 | 2.2 | 2.4 | 84 |
| 43 | 2 | 2.2 | 84 |
| 32 | 28 | 28 | — |
| 33 | 32 | 32 | — |
| 34 | 32 | 32 | — |
| 35 | 32 | 32 | — |
| 36 | 32 | 32 | — |
| 37 | 32 | 32 | — |
| 38 | 32 | 32 | — |
| 39 | 32 | 32 | — |
| 40 | 34 | 34 | — |
| 41 | 32 | 32 | — |

Accordingly, the results obtained using the testing procedures described above reveal that the alkoxylated sorbitan ester demulsifiers of the invention show comparable or improved performance relative to demulsifiers based on traditional chemistries or currently available commercial products. Furthermore, the results demonstrate that the demulsifiers of the invention are superior to ethoxylated sorbitan esters, sold commercially under the tradename TWEEN®.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. An alkoxylated sorbitan ester of formula (I), (I)

[structural formula]

wherein, $R^1$ is selected from the group consisting of alkyl, alkenyl, and alkynyl;

$R^2$, $R^3$, and $R^4$ are each independently selected from the group consisting of hydrogen, alkyl, alkenyl, and alkynyl;

$x_1+x_2+x_3=x=0.2$ to less than 1 or greater than 50 to 75; and $y_1+y_2+y_3=y=0$ or greater than 50 to 250.

2. The compound of claim 1, wherein $R^1$ is unsubstituted alkyl.

3. The compound of claim 1, wherein $R^1$ is unsubstituted alkyl selected from the group consisting of —$CH_2CH_3$; —$(CH_2)_2CH_3$; —$(CH_2)_3CH_3$; —$(CH_2)_4CH_3$; —$(CH_2)_5CH_3$; —$(CH_2)_6CH_3$; —$(CH_2)_7CH_3$; —$(CH_2)_8CH_3$; —$(CH_2)_9CH_3$; —$(CH_2)_{10}CH_3$; —$(CH_2)_{11}CH_3$; —$(CH_2)_{12}CH_3$; —$(CH_2)_{13}CH_3$; —$(CH_2)_{14}CH_3$; —$(CH_2)_{15}CH_3$; —$(CH_2)_{16}CH_3$; —$(CH_2)_{17}CH_3$; —$(CH_2)_{18}CH_3$; —$(CH_2)_{19}CH_3$; —$(CH_2)_{20}CH_3$; —$(CH_2)_{21}CH_3$; —$(CH_2)_{22}CH_3$; —$(CH_2)_{23}CH_3$; —$(CH_2)_{24}CH_3$; —$(CH_2)_{25}CH_3$; —$(CH_2)_{26}CH_3$; —$(CH_2)_{27}CH_3$; —$(CH_2)_{28}CH_3$; —$(CH_2)_{29}CH_3$; —$(CH_2)_{30}CH_3$; —$(CH_2)_{31}CH_3$; —$(CH_2)_{32}CH_3$; —$(CH_2)_{33}CH_3$; and —$(CH_2)_{34}CH_3$.

4. The compound of claim 1, wherein $R^1$ is —$(CH_2)_{10}CH_3$.

5. The compound of claim 4, wherein $R^2$, $R^3$, and $R^4$ are each independently hydrogen.

6. The compound of claim 1, wherein $R^1$ is unsubstituted alkenyl.

7. The compound of claim 1, wherein $R^1$ is unsubstituted alkenyl selected from the group consisting of —$(CH_2)_2$CH═CHCH$_2$CH═CHCH$_2$CH═CHCH$_2$CH═CHCH$_2$CH═CH(CH$_2$)$_4$CH$_3$; —$(CH_2)_2$CH═CHCH$_2$CH═CHCH═CHCH$_2$CH═CHCH$_2$CH═CHCH$_2$CH$_3$; —$(CH_2)_3$CH═CHCH$_2$CH═CHCH$_2$CH═CH(CH$_2$)$_7$CH$_3$; —$(CH_2)_3$CH═CHCH$_2$CH$_2$CH═CHCH$_2$CH═CH(CH$_2$)$_4$CH$_3$; —$(CH_2)_3$CH═CH(CH$_2$)$_4$CH═CHCH$_2$CH═CH(CH$_2$)$_4$CH$_3$; —$(CH_2)_3$CH═CHCH$_2$CH═CHCH$_2$CH═CH(CH$_2$)$_4$CH$_3$; —$(CH_2)_3$CH═CHCH$_2$CH═CHCH$_2$CH═CHCH$_2$CH$_3$; —$(CH_2)_3$CH═CHCH═CHCH═CHCH═CH(CH$_2$)$_4$CH$_3$; —$(CH_2)_4$CH═CH(CH$_2$)$_8$CH$_3$; —$(CH_2)_4$CH═CHCH$_2$CH═CHCH$_2$CH═CH(CH$_2$)$_4$CH$_3$; —$(CH_2)_4$CH═

CHCH$_2$CH=CHCH$_2$CH=CHCH$_2$CH=CHCH$_2$CH$_3$;
—(CH$_2$)$_4$CH=CHCH$_2$CH=CHCH$_2$CH=CHCH$_2$CH=
CHCH$_2$CH=CHCH$_2$CH$_3$;   —(CH$_2$)$_4$CH=CHCH$_2$CH=
CHCH$_2$CH=CHCH$_2$CH=CHCH$_2$CH=CH(CH$_2$)$_4$CH$_3$;
—(CH$_2$)$_4$CH=CHCH$_2$CH=CHCH$_2$CH=CHCH$_2$CH=
CHCH$_2$CH=CHCH$_2$CH=CHCH$_2$CH$_3$;   —(CH$_2$)$_5$CH=
CHCH$_2$CH=CHCH$_2$CH=CHCH$_2$CH$_3$;   —(CH$_2$)$_5$CH=
CHCH$_2$CH=CHCH$_2$CH=CHCH$_2$CH=CH(CH$_2$)$_4$CH$_3$;
—(CH$_2$)$_5$CH=CHCH$_2$CH=CHCH$_2$CH=CHCH$_2$CH=
CHCH$_2$CH=CHCH$_2$CH$_3$;   —(CH$_2$)$_6$CH=CHCH=
CHCH=CH(CH$_2$)$_4$CH$_3$;   —(CH$_2$)$_6$CH=CHCH$_2$CH=
CHCH$_2$CH=CHCH$_2$CH=CH(CH$_2$)$_4$CH$_3$; —(CH$_2$)$_7$CH=
CH(CH$_2$)$_3$CH$_3$;   —(CH$_2$)$_7$CH=CH(CH$_2$)$_5$CH$_3$;   —(CH$_2$)$_7$
CH=CH(CH$_2$)$_7$CH$_3$; —(CH$_2$)$_7$CH=CHCH=CHCH=CH
(CH$_2$)$_3$CH$_3$;   —(CH$_2$)$_7$CH=CHCH=CH(CH$_2$)$_5$CH$_3$;
—(CH$_2$)$_7$CH=CHCH$_2$CH=CH(CH$_2$)$_4$CH$_3$;   —(CH$_2$)$_7$
CH=CHCH$_2$CH=CH(CH$_2$)$_4$CH$_3$;   —(CH$_2$)$_7$CH=
CHCH=CHCH$_2$CH$_2$CH=CHCH$_2$CH$_3$;   —(CH$_2$)$_7$
CH=CHCH=CHCH=CHCH=CHCH$_2$CH$_3$;   —(CH$_2$)$_7$
CH=CHCH$_2$CH=CHCH$_2$CH=CHCH$_2$CH=CH(CH$_2$)$_4$
CH$_3$;   —(CH$_2$)$_7$CH=CHCH$_2$CH=CHCH$_2$CH=
CHCH$_2$CH$_3$;   —(CH$_2$)$_7$CH=CHCH$_2$CH=CHCH$_2$CH=
CHCH$_2$CH=CHCH$_2$CH=CHCH$_2$CH$_3$;   —(CH$_2$)$_9$CH=
CH(CH$_2$)$_5$CH$_3$;   —(CH$_2$)$_9$CH=CHCH$_2$CH=CH(CH$_2$)$_4$
CH$_3$;   —(CH$_2$)$_9$CH=CHCH$_2$CH=CHCH$_2$CH=CHCH$_2$
CH$_3$; —(CH$_2$)$_9$CH=CH(CH$_2$)$_7$CH$_3$; —(CH$_2$)$_{11}$CH=CH
(CH$_2$)$_5$CH$_3$;   —(CH$_2$)$_{11}$CH=CH(CH$_2$)$_7$CH$_3$;   —(CH$_2$)$_{11}$
CH=CHCH$_2$CH=CH(CH$_2$)$_4$CH$_3$; and —(CH$_2$)$_{13}$CH=CH
(CH$_2$)$_7$CH$_3$.

8. The compound of claim 1, wherein R$^1$ is —(CH$_2$)$_7$CH=CH(CH$_2$)$_7$CH$_3$.

9. The compound of claim 8, wherein R$^2$, R$^3$, and R$^4$ are each independently hydrogen.

10. A process for preparing a compound of claim 1 wherein R$^2$, R$^3$, and R$^4$ are each independently hydrogen, the process comprising:
treating a sorbitan ester of formula (1) with x equivalents of propylene oxide of formula (2) to provide a propoxylated sorbitan ester of formula (3),

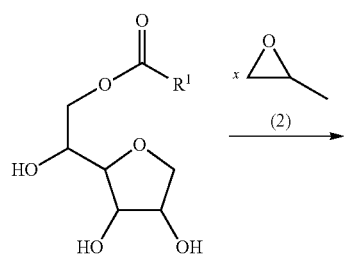

(1)

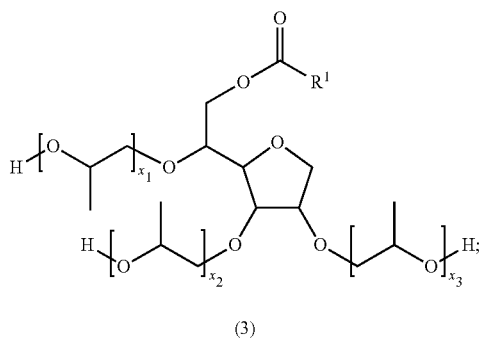

(3)

and treating the compound of formula (3) with y equivalents of ethylene oxide of formula (4) to provide a compound of formula (I),

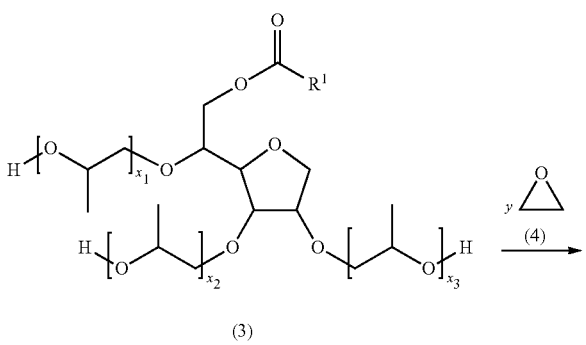

(3)

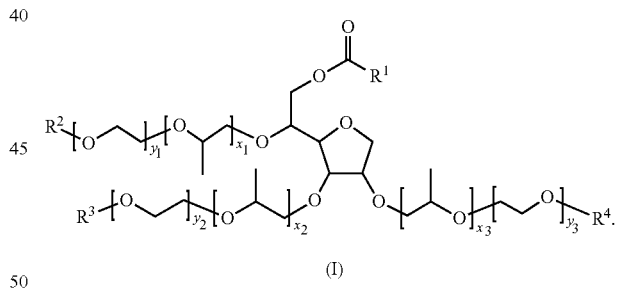

(I)

* * * * *